United States Patent
Evans et al.

(10) Patent No.: US 11,542,309 B2
(45) Date of Patent: Jan. 3, 2023

(54) FIBROBLAST GROWTH FACTOR 1 (FGF1) MUTANT PROTEINS THAT SELECTIVELY ACTIVATE FGFR1B TO REDUCE BLOOD GLUCOSE

(71) Applicant: Salk Institute for Biological Studies, La Jolla, CA (US)

(72) Inventors: Ronald M. Evans, La Jolla, CA (US); Michael Downes, San Diego, CA (US); Annette Atkins, San Diego, CA (US); Sihao Liu, San Diego, CA (US); Ruth T. Yu, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 16/929,342

(22) Filed: Jul. 15, 2020

(65) Prior Publication Data

US 2021/0032303 A1  Feb. 4, 2021

Related U.S. Application Data

(60) Provisional application No. 62/880,853, filed on Jul. 31, 2019.

(51) Int. Cl.
| | |
|---|---|
| *C07K 14/50* | (2006.01) |
| *A61P 3/10* | (2006.01) |
| *A61K 9/00* | (2006.01) |
| *A61K 45/06* | (2006.01) |
| *A61K 38/00* | (2006.01) |

(52) U.S. Cl.
CPC ............... *C07K 14/50* (2013.01); *A61P 3/10* (2018.01); *A61K 9/0019* (2013.01); *A61K 38/00* (2013.01); *A61K 45/06* (2013.01)

(58) Field of Classification Search
CPC ............ C07K 14/50; A61K 38/00; A61P 3/10
See application file for complete search history.

(56) References Cited

U.S. PATENT DOCUMENTS

| | | | |
|---|---|---|---|
| 5,132,408 A | 7/1992 | Baird et al. |
| 5,478,804 A | 12/1995 | Calabresi et al. |
| 5,656,458 A | 8/1997 | Barr |
| 5,658,889 A | 8/1997 | Gruber et al. |
| 5,693,775 A | 12/1997 | Nathans et al. |
| 5,885,960 A | 3/1999 | Nies |
| 6,326,484 B1 | 12/2001 | Gage et al. |
| 6,800,286 B1 | 10/2004 | Olwin et al. |
| 6,982,170 B1 | 1/2006 | Maciag et al. |
| 7,491,697 B2 | 2/2009 | Beals et al. |
| 7,582,607 B2 | 9/2009 | Frye et al. |
| 7,595,296 B1 | 9/2009 | Blaber et al. |
| 7,622,445 B2 | 11/2009 | Frye et al. |
| 7,655,627 B2 | 2/2010 | Frye et al. |
| 7,700,558 B2 | 4/2010 | Thomason et al. |
| 7,723,050 B2 | 5/2010 | Urdea et al. |
| 7,776,825 B1 | 8/2010 | Blaber et al. |
| 7,790,682 B1 | 9/2010 | Blaber et al. |
| 7,956,033 B2 | 6/2011 | Cheng et al. |
| 8,053,408 B2 | 11/2011 | Thomason et al. |
| 8,062,632 B2 | 11/2011 | Lee et al. |
| 8,168,591 B2 | 5/2012 | Takada et al. |
| 8,372,952 B2 | 2/2013 | Smith et al. |
| 8,529,940 B2 | 9/2013 | Sunvold et al. |
| 8,535,912 B2 | 9/2013 | Sonoda |
| 8,642,546 B2 | 2/2014 | Belouski et al. |
| 8,889,426 B2 | 11/2014 | Mohammadi et al. |
| 8,889,621 B2 | 11/2014 | Mohammadi et al. |
| 8,906,854 B2 | 12/2014 | Jonker et al. |
| 8,951,966 B2 | 2/2015 | Ling et al. |
| 8,999,929 B2 | 4/2015 | Mohammadi et al. |
| 9,072,708 B2 | 7/2015 | Jonker et al. |
| 9,272,017 B2 | 3/2016 | Mohammadi et al. |
| 9,446,097 B2 | 9/2016 | Jonker et al. |
| 9,464,126 B2 | 10/2016 | Mohammadi et al. |
| 9,474,785 B2 | 10/2016 | Mohammadi et al. |
| 9,808,508 B2 | 11/2017 | Jonker et al. |
| 9,925,241 B2 | 3/2018 | Suh et al. |
| 9,925,243 B2 | 3/2018 | Suh et al. |
| 10,159,711 B2 | 12/2018 | Jonker et al. |
| 10,293,027 B2 | 5/2019 | Jonker et al. |
| 10,398,759 B2 | 9/2019 | Jonker et al. |
| 10,695,404 B2 | 6/2020 | Evans et al. |
| 2003/0008820 A1 | 1/2003 | Kwan et al. |
| 2004/0082564 A1 | 4/2004 | Arrhenius et al. |
| 2004/0259780 A1 | 12/2004 | Glasebrook et al. |

(Continued)

FOREIGN PATENT DOCUMENTS

| | | |
|---|---|---|
| CN | 1890371 A | 1/2007 |
| EP | 0 420 222 A1 | 4/1991 |

(Continued)

OTHER PUBLICATIONS

Bowie et al., Science 247: 1306-1310, (1990).*
Wells, Biochemistry 29:8509-8517, (1990).*
Accession No. 1605206A, Sep. 14, 1996.
Abraham et al., "Human Basic Fibroblast Growth Factor: Nucleotide Sequence and Genomic Organization," *EMBO J.* 5(10): 2523-2528, 1986.
Adams et al., "LY2405319, an Engineered FGF21 Variant, Improves the Metabolic Status of Diabetic Monkeys," *PLoS One* 8:e65763, 2013.
Andrukhova et al., "FGF23 Acts Directly on Renal Proximal Tubules to Induce Phosphaturia Through Activation of the ERK1/2-SKG1 Signaling Pathway," *Bone* 51:621-628, 2012.

(Continued)

Primary Examiner — Gyan Chandra
(74) Attorney, Agent, or Firm — Klarquist Sparkman, LLP

(57) ABSTRACT

The present disclosure provides FGF1 mutant proteins, which selectively bind to/activate FGFR1b. Also provided are nucleic acid molecules that encode such proteins, and vectors and cells that include such nucleic acids. Methods of using the disclosed FGF1 mutants to reduce blood glucose in a mammal and treat a metabolic disorder are provided.

20 Claims, 9 Drawing Sheets

Specification includes a Sequence Listing.

(56) References Cited

U.S. PATENT DOCUMENTS

| | | |
|---|---|---|
| 2006/0217310 A1 | 9/2006 | Chiu et al. |
| 2007/0099834 A1 | 5/2007 | Takada et al. |
| 2007/0142278 A1 | 6/2007 | Beals et al. |
| 2007/0237768 A1 | 10/2007 | Glaesner et al. |
| 2007/0265200 A1 | 11/2007 | Glaesner et al. |
| 2007/0293430 A1 | 12/2007 | Frye et al. |
| 2007/0299007 A1 | 12/2007 | Frye et al. |
| 2008/0103096 A1 | 5/2008 | Frye et al. |
| 2008/0176790 A1 | 7/2008 | DeFrees |
| 2008/0255045 A1 | 10/2008 | Cujec et al. |
| 2008/0260703 A1 | 10/2008 | Riordan et al. |
| 2008/0261875 A1 | 10/2008 | Etgen et al. |
| 2009/0111742 A1 | 4/2009 | Kharitonenkov et al. |
| 2009/0118190 A1 | 5/2009 | Beals et al. |
| 2009/0305986 A1 | 12/2009 | Belouski et al. |
| 2010/0062984 A1 | 3/2010 | Kumar et al. |
| 2010/0158914 A1 | 6/2010 | Desnoyers |
| 2010/0184665 A1 | 7/2010 | Suzuki et al. |
| 2010/0216715 A1 | 8/2010 | Tagmose et al. |
| 2010/0285131 A1 | 11/2010 | Belouski et al. |
| 2010/0286042 A1 | 11/2010 | Imamura et al. |
| 2010/0323954 A1 | 12/2010 | Li et al. |
| 2011/0046091 A1 | 2/2011 | Cau et al. |
| 2011/0053841 A1 | 3/2011 | Yayon et al. |
| 2011/0104152 A1 | 5/2011 | Sonoda |
| 2011/0150901 A1 | 6/2011 | Smith et al. |
| 2011/0172401 A1 | 7/2011 | Cujec et al. |
| 2011/0190207 A1 | 8/2011 | Mohammadi et al. |
| 2011/0195077 A1 | 8/2011 | Glass et al. |
| 2012/0052069 A1 | 3/2012 | Belouski et al. |
| 2012/0288886 A1 | 11/2012 | Mohammadi et al. |
| 2012/0302491 A1 | 11/2012 | Narkar et al. |
| 2013/0023474 A1 | 1/2013 | Ling et al. |
| 2013/0058896 A1 | 3/2013 | Takada et al. |
| 2013/0116171 A1 | 5/2013 | Jonker et al. |
| 2013/0130983 A1 | 5/2013 | Blaber et al. |
| 2013/0184211 A1 | 7/2013 | Mohammadi et al. |
| 2013/0197191 A1 | 8/2013 | Smith et al. |
| 2013/0231277 A1 | 9/2013 | Mohammadi et al. |
| 2013/0331316 A1 | 12/2013 | Mohammadi et al. |
| 2013/0331317 A1 | 12/2013 | Mohammadi et al. |
| 2013/0331325 A1 | 12/2013 | Mohammadi et al. |
| 2014/0045751 A1 | 2/2014 | Blaber |
| 2014/0094406 A1 | 4/2014 | Mohammadi et al. |
| 2014/0107022 A1 | 4/2014 | Mohammadi et al. |
| 2014/0155316 A1 | 6/2014 | Mohammadi et al. |
| 2014/0171361 A1 | 6/2014 | Jonker et al. |
| 2014/0243260 A1 | 8/2014 | Mohammadi et al. |
| 2015/0065419 A1 | 3/2015 | Jonker et al. |
| 2015/0079003 A1 | 3/2015 | Brentnall et al. |
| 2015/0111821 A1 | 4/2015 | Suh et al. |
| 2015/0343022 A1 | 12/2015 | Jonker et al. |
| 2015/0361436 A1 | 12/2015 | Hitchcock et al. |
| 2016/0206695 A1 | 7/2016 | Suh et al. |
| 2016/0237133 A1 | 8/2016 | Suh et al. |
| 2016/0354440 A1 | 12/2016 | Jonker et al. |
| 2017/0056475 A1 | 3/2017 | Jonker et al. |
| 2017/0291931 A1 | 10/2017 | Evans et al. |
| 2017/0355739 A1 | 12/2017 | Evans et al. |
| 2017/0355740 A1 | 12/2017 | Evans et al. |
| 2018/0036377 A1 | 2/2018 | Jonker et al. |
| 2018/0050087 A1 | 2/2018 | McDonnell et al. |
| 2018/0057554 A1 | 3/2018 | Evans et al. |
| 2018/0200334 A1 | 7/2018 | Jonker et al. |
| 2018/0228869 A1 | 8/2018 | Evans et al. |
| 2019/0151416 A1 | 5/2019 | Evans et al. |
| 2019/0192630 A1 | 6/2019 | Suh et al. |
| 2019/0358296 A1 | 11/2019 | Jonker et al. |
| 2020/0040051 A1 | 2/2020 | Evans et al. |

FOREIGN PATENT DOCUMENTS

| | | |
|---|---|---|
| EP | 0 645 451 | 8/2001 |
| JP | 4-164096 | 6/1992 |
| JP | 2013-525309 | 6/2013 |
| WO | WO 2002/036732 A2 | 5/2002 |
| WO | WO 2003/052378 A2 | 6/2003 |
| WO | WO 2004/003179 A1 | 1/2004 |
| WO | WO 2004/108167 A1 | 12/2004 |
| WO | WO 2005/063 807 A2 | 7/2005 |
| WO | WO 2006/028714 A1 | 3/2006 |
| WO | WO 2008/038287 A2 | 4/2008 |
| WO | WO 2008/047235 A2 | 4/2008 |
| WO | WO 2010/075037 A1 | 7/2010 |
| WO | WO 2010/129600 A2 | 11/2010 |
| WO | WO 2010/135491 A2 | 11/2010 |
| WO | WO 2011/047267 A1 | 4/2011 |
| WO | WO 2011/068893 A1 | 6/2011 |
| WO | WO 2011/130729 A2 | 10/2011 |
| WO | WO 2012/010553 A1 | 1/2012 |
| WO | WO 2012/062078 A1 | 5/2012 |
| WO | WO 2012/066075 A1 | 5/2012 |
| WO | WO 2012/140650 A2 | 10/2012 |
| WO | WO 2013/006486 A2 | 1/2013 |
| WO | WO 2013/033452 A2 | 3/2013 |
| WO | WO 2013/090919 A1 | 6/2013 |
| WO | WO 2013/131091 A1 | 9/2013 |
| WO | WO 2013/184958 A1 | 12/2013 |
| WO | WO 2013/184960 A2 | 12/2013 |
| WO | WO 2013/184962 A1 | 12/2013 |
| WO | WO 2014/085365 A2 | 6/2014 |
| WO | WO 2015/061331 A1 | 4/2015 |
| WO | WO 2015/061351 A1 | 4/2015 |
| WO | WO 2015/061361 A1 | 4/2015 |
| WO | WO 2015/065897 A1 | 5/2015 |
| WO | WO 2015/149069 A1 | 10/2015 |
| WO | WO 2015/183890 A2 | 12/2015 |
| WO | WO 2015/198175 A1 | 12/2015 |
| WO | WO 2016/089945 A1 | 6/2016 |
| WO | WO 2016/172153 A2 | 10/2016 |
| WO | WO 2016/172156 A2 | 10/2016 |
| WO | WO 2016/172290 A1 | 10/2016 |
| WO | WO 2017/075260 A1 | 5/2017 |
| WO | WO 2018/018010 A1 | 1/2018 |
| WO | WO 2018/026713 A1 | 2/2018 |

OTHER PUBLICATIONS

Beenken & Mohammadi, "The Structural Biology of the FGF19 Subfamily," *Adv Exp Med Biol.* 728:1-24, 2012.

Beenken and Mohammadi, "The FGF Family: Biology, Pathophysiology and Therapy," *Nat Rev Drug Discov.* 8:235-253, 2009.

Beenken et al., "Plasticity in Interactions of Fibroblast Growth Factor 1 (FGF1) N Terminus With FGF Receptors Underlies Promiscuity of FGF1," *J Biol Chem.* 287:3061-3013, 2012.

Beenken, "Structural and biochemical Studies of FGF-FGFR Complexes," Thesis, Sep. 2011.

Blaber et al., "Accelerated healing in NONcNZO10/LtJ type 2 diabetic mice by FGF-1," *Wound Repair Regeneration* 23:538-549, 2015.

Bossard et al., "Translokin is an Intracellular Mediator of FGF-2 Trafficking," *Nat Cell Biol.* 5:433-439, 2003.

Brewster et al., "Heparin-independent mitogenicity in an endothelial and smooth muscle cell chimeric growth factor (S130K-HBGAM)," *Am J Surg.* 188:515-519, 2004.

Brewster et al., "Improving endothelial healing with novel chimeric mitogens," *Am J Surg.* 192:589-593, 2006.

Brych et al., "Structure and Stability Effects of Mutations Designed to Increase the Primary Sequence Symmetry Within the Core Region of a β-Trefoil," *Prot Sci.* 10:2587-2599, 2001.

Cassidy et al., "Elevated Frequency of Diabetes Mellitus in Hospitalized Manic-Depressive Patients," *Am J Psychiatry* 156:1417-1420, 1999.

Czajkowsky et al., "Fc-Fusion Proteins: New Developments and Future Perspectives," *EMBO Mol Med.* 4:1015-1028, 2012.

Dubey et al., "Spackling the Crack: Stabilizing Human Fibroblast Growth Factor-1 by Targeting the N and C Terminus β-Strand Interactions," *J Mol Biol.* 371:256-268, 2007.

Dutchak et al., "Fibroblast Growth Factor-21 Regulates PPARγ Activity and the Antidiabetic Actions of Thiazolidinediones," *Cell* 148:556-561, 2012.

(56) References Cited

OTHER PUBLICATIONS

Esch et al., "Primary Structure of Bovine Pituitary Basic Fibroblast Growth Factor (FGF) and Comparison with the Amino-Terminal Sequence of Bovine Brain Acidic FGF," *PNAS* 82:6507-6511, 1985.
Fathallah et al., "Drug-Induced Hyperglycaemia and Diabetes," *Drug Safety* 38:1153-1168, 2015.
Finan et al., "A Rationally Designed Monomeric Peptide Triagonist Corrects Obesity and Diabetes in Rodents," *Nat Med.* 21:27-36, 2015.
Fowler, "Diabetes Treatment, Part 2: Oral Agents for Glycemic Management," *Clin. Diabetes* 25:131-134, 2007.
Ge et al., "Characterization of a FGF19 Variant with Altered Receptor Specificity Revealed a Central Role for FGFR1c in the Regulation of Glucose Metabolism," *PloS ONE* 7:e33603, 2012.
Goetz et al., "Conversion of a Paracrine Fibroblast Growth Factor into an Endocrine Fibroblast Growth Factor," *J Biol Chem.* 287:29134-29146, 2012.
Goetz et al., "Isolated C-Terminal Tail of FGF23 Alleviates Hypophosphatemia by Inhibiting FGF23-FGFR-Klotho Complex Formation," *Proc Natl Acad Sci USA* 107:407-412, 2010.
Goetz et al., "Klotho Coreceptors Inhibit Signaling by Paracrine Fibroblast Growth Factor 8 Subfamily Ligands," *Mol Cell Biol.* 32:1944-1954, 2012.
Goetz et al., "Molecular Insights Into the Klotho-Dependent, Endocrine Mode of Action of Fibroblast Growth Factor 19 Subfamily Members," *Mol Cell Biol.* 27:3417-3428, 2007.
Grieb et al., "Primary structure of ovine fibroblast growth factor-1 deduced by protein and cDNA analysis," *Biochem Biophys Res Commun.* 246:182-191, 1998.
Guo et al., "Risk of Diabetes Mellitus Associated With Atypical Antipsychotic Use Among Patients With Bipolar Disorder: A Retrospective, Population-Based, Case-Control Study," *J Clin. Psychiatry* 67:1055-1061, 2006.
Harmer et al., "Towards a resolution of the stoichiometry of the fibroblast growth factor (FGF)-FGF receptor-heparin complex," *J Mol Biol.* 339:821-834, 2004.
Hevener et al., "Muscle-Specific Pparg Deletion Causes Insulin Resistance," *Nat Med.* 9:1491-1497 (2003).
Hutley et al., "Fibroblast Growth Factor 1," *Diabetes* 53:3097-3106, 2004.
Hwang and Weis, "Steroid-Induced Diabetes: A Clinical and Molecular Approach to Understanding and Treatment," *Diabetes Metab Res Rev.* 30:96-102, 2014.
Igarashi et al., "Characterization of Recombinant Human Fibroblast Growth Factor (FGF)-10 Reveals Functional Similarities with Keratinocyte Growth Factor (FGF-7)," *J Biol Chem.* 273:13230-13235, 1998.
Ikezono and Hanai, "The Effect of Satiation of the Acidic Fibroblast Growth Factor-Like Activity on Ingestion of Soyamalt and Soybean Milk"; *Int J Obesity* 25(S2):S142, 2001. Abstract P403.
Imamura et al., "Identification of the Domain Within Fibroblast Growth Factor-1 Responsible for Heparin-Dependence," *Biochim Biophys Acta.* 1266:124-130, 1995.
Imamura et al., "Recovery of Mitogenic Activity of a Growth Factor Mutant with a Nuclear Translocation Sequence," *Science* 249:1561-1510, 1990.
Inchovska et al., "Fibroblast Growth Factors Promote Pancreatic Cell Proliferation in Normal and STZ-Treated Hamsters," *Arch Med Sci.* 2:90-93, 2006.
Inchovska et al., "Role of FGF1, FGF2 and FGF7 in the Development of the Pancreas of Diabetic Hamsters," *Acta morphologica et anthropologica* 12:79-85, 2007.
Inchovska et al., "Role of FGF1, FGF2, FGF7 in the Development of Pancreas from Control and Streptozotocin-Treated Hamsters," *Cell Proliferation* 39:537-550, 2006.
Irwin et al., "A Novel CCK-8/GLP-1 Hybrid Peptide Exhibiting Prominent Insulinotropic, Glucose-Lowering, and Satiety Actions With Significant Therapeutic Potential in High-Fat-Fed Mice," *Diabetes* 64:2996-3009, 2015.

Itoh and Ornitz, "Fibroblast Growth Factors: From Molecular Evolution to Roles in Development, Metabolism and Disease," *J Biochem.* 149:121-130, 2011.
Jonker et al., "A PPARγ-FGF1 Axis is Required for Adaptive Adipose Remodelling and Metabolic Homeostasis," *Nature* 485:391-394, 2012.
Kharitonenkov et al., "FGF-21/FGF-21 Receptor Interaction and Activation is Determined by βKlotho," *J Cell Physiol.* 215:1-7, 2008.
Kharitonenkov et al., "FGF-21 as a Novel Metabolic Regulator," *J Clin Invest.* 115:1627-1635, 2005.
Kharitonenkov et al., "The Metabolic State of Diabetic Monkeys is Regulated by Fibroblast Growth Factor-21," *Endocrinology* 148:774-781, 2007.
Kharitonenkov and DiMarchi, "Break on Through to the Other 1," *Cell Metabolism* 20:554-555, 2014.
Kilkenny et al.; "Fibroblast Growth Factor Receptor-1 Signaling in Pancreatic Islet Beta-Cells is Modulated by the Extracellular Matrix," *Mol EndocrinoL.* 22:196-205, 2008.
Klingenberg et al., "Effects of Mutations of a Phosphorylation Site in an Exposed Loop in Acidic Fibroblast Growth Factor," *J Biol Chem.* 274:18081-18086, 1999.
Kobielak et al., "Protease Resistant Variants of FGF1 with Prolonged Biological Activity," *Protein Pept Lett.* 21:434-443, 2014.
Kurosu et al., "The Klotho Gene Family as a Regulator of Endocrine Fibroblast Growth Factors," *Mol Cell Endocrin.* 299:72-78,2009.
Kurosu et al., "Tissue-Specific Expression of βKlotho and Fibroblast Growth Factor (FGF) Receptor Isoforms Determines Metabolic Activity of FGF19 and FGF21," *J Biol Chem.* 282:26687-26695, 2007.
Lee and Blaber, "Structural Basis of Conserved Cysteine in the Fibroblast Growth Factor Family: Evidence for a Vestigial Half-Cysteine," *J Mol Biol.* 393:128-139, 2009.
Lee and Blaber, "The Interaction Between Thermodynamic Stability and Buried Free Cysteines in Regulating the Functional Half-Life of Fibroblast Growth Factor-1," *J Mol Biol.* 393:113-127, 2009.
Lehrke and Lazar, "The Many Faces of PPARγ," *Cell* 123:993-999, 2005.
Li et al., "Strong Suppression of Feeding by a Peptide Containing Both the Nuclear Localization Sequence of Fibroblast Growth Factor-1 and a Cell Membrane-Permeable Sequence," *Neuroscience Lett.* 255:41-44, 1998.
Lin et al., "Role of the Nuclear Localization Sequence in Fibroblast Growth Factor-1-Stimulated Mitogenic Pathways," *J Biol Chem.* 271:5305-5308, 1996.
Liu et al., "Effective Treatment of Steatosis and Steatohepatitis by Fibroblast Growth Factor 1 in Mouse Models of Nonalcoholic Fatty Liver Disease," *Proc Natl Acad Sci USA* 113:2288-2293, 2016.
Longo et al., "Experimental support for the foldability—function tradeoff hypothesis: Segregation of the folding nucleus and functional regions in fibroblast growth factor-1," *Protein Sci.* 21:1911-1920, 2012.
Luo et al., "A Nontumorigenic Variant of FGF19 Treats Cholestatic Liver Diseases," *Sci Transl Med.* 6:247ra100, 2014.
Micanovic et al., "Different Roles of N-and C-Termini in the Functional Activity of FGF21," *J Cell Physiol.* 219:227-234, 2009.
Mohammadi et al., "Structural Basis for Fibroblast Growth Factor Receptor Activation," *Cytokine Growth Factor Rev.* 16:107-137, 2005.
Mori et al., "Direct Binding of Integrin αvβ3 to FGF1 Plays a Role in FGF1 Signaling," *J Biol Chem* 283:18066-18075, 2008.
Motomura et al., "An FGF1:FGF2 Chimeric Growth Factor Exhibits Universal FGF Receptor Specificity, Enhanced Stability and Augmented Activity Useful for Epithelial Proliferation and Radioprotection," *Biochim Biophys Acta.* 1780:1432-1440, 2008.
Nakayama et al., "Post Treatment With an FGF Chimeric Growth Factor Enhances Epithelial Cell Proliferation to Improve Recovery From Radiation-Induced Intestinal Damage," *Int J Radiat Oncol Biol Phys.* 78:860-867, 2010.
Niu et al., "Solid-Phase Polyethylene Glycol Conjugation Using Hydrophobicinteraction Chromatography," *J Chromatogr. A* 1327:66-72, 2014.

(56) References Cited

OTHER PUBLICATIONS

Ogneva et al., "The Effect of In Vitro Fibroblast Growth Factors on Cell Proliferation in Pancreas from Normal and Streptozoticin-Treated Rats," *Diabetes Res Clin Practice* 57:11-16, 2002.
O'Harte et al., "Novel Dual Agonist Peptide Analogues Derived From Dogfish Glucagon Show Promising in vitro Insulin Releasing Actions and Antihyperglycaemic Activity in Mice," *Mol Cell Endocrinol.* 431:133-144, 2016.
Ohta and Itoh, "Roles of FGFs as Adipokines in Adipose Tissue Development, Remodeling, and Metabolism," Frontiers in Endocrinology, vol. 5, No. FEB, Article 18, pp. 1-4, 2014.
Olsen et al., "Insights Into the Molecular Basis for Fibroblast Growth Factor Receptor Autoinhibition and Ligand-Binding Promiscuity," *Proc Natl Acad Sci. USA* 101:935-940, 2004.
Ono et al., "Novel Regulation of Fibroblast Growth Factor 2 (FGF2)-Mediated Cell Growth by Polysialic Acid," *J Biol Chem.* 287:3710-3722, 2012.
Perez et al., "Glucocorticoid-induced hyperglycemia," *J. Diabetes* 6:9-20, 2014.
Poa and Edgar, "Insulin Resistance Is Associated With Hypercortisolemia in Polynesian Patients Treated With Antipsychotic Medication," *Diabetes Care* 30:1425-1429, 2007.
Presta et al., "Structure-Function Relationship of Basic Fibroblast Growth Factor: Site-Directed Mutagenesis of a Putative Heparin-Binding and Receptor-Binding Region," *Biochem Biophys Res Commun.* 185:1098-1107, 1992.
Rafacho et al., "Glucocorticoid Treatment and Endocrine Pancreas Function: Implications for Glucose Homeostasis, Insulin Resistance and Diabetes," *J Endocrinol.* 223:R49-R62, 2014.
Razzaque, "The FGF23-Klotho Axis: Endocrine Regulation of Phosphate Homeostasis," *Nat Rev Endocrinol.* 5:611-619, 2009.
Reid, "Choosing GLP-1 Receptor Agonists or DPP-4 Inhibitors: Weighing the Clinical Trial Evidence," *Clin. Diabetes* 30:3-12, 2012.
Ripsin et al., "Management of Blood Glucose in Type 2 Diabetes Mellitus," *Am Fam. Physician* 79:29-36, 2009.
Royce et al., "Incorporation of polymer microspheres within fibrin scaffolds for the controlled delivery of FGF-1," *J Biomater Sci Polymer Edn.* 15:1327-1336, 2004.
Sasaki et al., "Effects of Fibroblast Growth Factors and Related Peptides on Food Intake by Rats," *Physiol Behav.* 56:211-218, 1994.
Schlessinger et al., "Crystal Structure of a Ternary FGF-FGFR-Heparin Complex Reveals a Dual Role for Heparin in FGFR Binding and Dimerization," *Mol. Cell* 6:743-750, 2000.
Sequence Identity BLAST, Feb. 23, 2015.
Shireman et al., "The S130K fibroblast growth factor-1 mutant induces heparin-independent proliferation and is resistant to thrombin degradation in fibrin glue," *J Vasc Surg.* 31:382-390, 2000.
Smith et al., "FGF21 Can Be Mimicked In Vitro and In Vivo by a Novel Anti-FGFR1c/b-Klotho Bispecific Protein," *PLoS ONE* 8:e61432, 2013.
Storz et al., "Intellectual Property Issues Therapeutics, Vaccines and Molecular Diagnostics," Springer Science & Business Media, May 11, 2012.
Suh et al., "Endocrinization of FGF1 Produces a Neomorphic and Potent Insulin Sensitizer," *Nature* 513:436-439, 2014.
Sun and Scherer, "The PPARγ-FGF1 Axis: An Unexpected Mediator of Adipose Tissue Homeostasis," *Cell Res.* 22:1416-1418, 2012.
Suzuki et al., "Feeding Suppression by Fibroblast Growth Factor-1 is Accompanied by Selective Induction of Heat Shock Protein 27 in Hypothalamic Astrocytes," *Eur J Neurosci.* 13:2299-2308, 2001.
Tamez-Perez et al., "Steroidhyperglycemia: Prevalence, early detection and therapeutic recommendations: A narrative review," *World J. Diabetes* 6:1073-1081, 2015.
Thompson et al., "Energetic Characterization of the Basic Fibroblast Growth Factor-Heparin Interaction: Identification of the Heparin Binding Domains," *Biochem.* 33:3831-3840, 1994.
Van Dijk et al., "Quantification of Hepatic Carbohydrate Metabolism in Conscious Mice Using Serial Blood and Urine Spots," *Anal Biochem.* 322:1-13, 2003.

Van Raalte & Diamant, "Steroid diabetes: from mechanism to treatment?," *Neth J Med.* 72:62-72, 2014.
Wang et al., "A Novel Monoclonal Antibody to Fibroblast Growth Factor 2 Effectively Inhibits Growth of Hepatocellular Carcinoma Xenografts," *Mol Cancer Ther.* 11:864-872, 2012.
Wei et al., "Fibroblast Growth Factor 21 Promotes Bone Loss by Potentiating the Effects of Peroxisome Proliferator-Activated Receptor γ," Proc Natl Acad Sci. USA 109:3143-3148, 2012.
Widberg et al., "Fibroblast Growth Factor Receptor 1 is a Key Regulator of Early Adipogenic Events in Human Preadipocytes"; *Am J Physiol Endocrinol Metab.* 296:E121-E131, 2009.
Wong et al., "*Analysis of Putative Heparin-binding Domains of Fibroblast Growth Factor-1,*" J Biol Chem. 270:25805-25811, 1995.
Wu et al., "C-Terminal Tail of FGF19 Determines Its Specificity Toward Klotho Co-Receptors," *J Biol Chem.* 283:33304-33309, 2008.
Wu et al., "Selective Activation of FGFR4 by an FGF19 Variant Does Not Improve Glucose Metabolism in ob/ob Mice," *Proc Natl Acad Sci. USA* 106:14379-14384, 2009.
Wu et al., "FGF19-Induced Hepatocyte Proliferation is Mediated Through FGFR4 Activation," *J Biol Chem.* 285:5165-5170, 2010.
Wu et al., "Separating Mitogenic and Metabolic Activities of Fibroblast Growth Factor 19 (FGF19)," *Proc Natl Acad Sci U.S.A.* 107:14158-14163, 2010.
Wu et al., "Amelioration of Type 2 Diabetes by Antibody-Mediated Activation of Fibroblast Growth Factor Receptor 1," *Sci Transl Med.* 3:113ra126, 2011.
Wu et al., "FGF19 Regulates Cell Proliferation, Glucose and Bile Acid Metabolism via FGFR4-Dependent and Independent Pathways," *PLoS One* 6:e17868, 2011.
Wu et al., "A Unique FGF23 With the Ability to Activate FGFR Signaling Through Both αKlotho and βKlotho," *J Mol Biol.* 418:82-89, 2012.
Wu and Li, "Chapter 13—Understanding The Structure-Function Relationship Between Fgf19 And Its Mitogenic And Metabolic Activities," in *Endocrine FGFs and Klothos*, Makoto Kuro-o (ed.), pp. 195-213, Landes Bioscience and Springer Science+Business Media, 2012.
Xia et al., "Pharmacokinetic Properties of 2nd-Generation Fibroblast Growth Factor-1 Mutants for Therapeutic Application," *PLoS One* 7:e48210, 2012.
Xia et al., "An S116R Phosphorylation Site Mutation in Human Fibroblast Growth Factor-1 Differentially Affects Mitogenic and Glucose-Lowering Activities," J Pharm Sci. 105:3507-3519, 2016.
Yao et al., "Expression and Pharmacological Evaluation of Fusion Protein FGF21-L-Fc," *Acta Pharmaceutica Sinica* 46:787-792, 2011 (with English abstract).
Yie et al., "FGF21 N-and C-Termini Play Different Roles in Receptor Interaction and Activation," *FEBS Lett.* 583:19-24, 2009.
Youseff et al., "Diabetes Mellitus, Obesity, and Hepatic Steatosis," *Semin Gastrointest Dis.* 13:17-30, 2002.
Zadeh et al., "The Liver Diseases of Lipodystrophy: The Long-term Effect of Leptin Treatment," *J Hepatol.* 59:131-137, 2013.
Zakrzewska et al., "Design of Fully Active FGF-1 Variants with Increased Stability," *Protein Eng Des Sel.* 17:603-611, 2004.
Zakrzewska et al., "Highly stable mutants of human fibroblast growth factor-1 exhibit prolonged biological action," *J Mol Biol.* 352:860-875, 2005.
Zakrzewska et al., "Increased Protein Stability of FGF1 Can Compensate for Its Reduced Affinity for Heparin," *J Biol Chem.* 284:25388-25403, 2009.
Zhang et al., "Receptor Specificity of the Fibroblast Growth Factor Family: The Complete Mammalian FGF Family," *J Biol Chem.* 281:15694-15700, 2006.
Zhou et al., "Separating Tumorigenicity from Bile Acid Regulatory Activity for Endocrine Hormone FGF19," *Cancer Res.* 74:3306-3316, 2014.
Zhu et al., "Three-Dimensional Structures of Acidic and Basic Fibroblast Growth Factors," *Science* 251:90-93, 1991.
Zinn et al., "Imaging Tc-99m-Labeled FGF-1 Targeting in Rats," *Nucl Med Biol.* 27:407-414, 2000.

(56) References Cited

OTHER PUBLICATIONS

CA Application No. 2,875,790 Office Action dated Mar. 22, 2019 (4 pages).
CN 201380039848.9 Office Action dated Oct. 8, 2016 (with English Translation) (23 pages).
CN 201380039848.9 Office Action dated Jun. 8, 2017 (with English translation) (18 pages).
EP 11769740.9 Exam Report dated Jul. 13, 2018 (5 pages).
EP 11769740.9 European Search Report dated Dec. 5, 2013 (10 pages).
EP 11769740.9 Office Action dated Jul. 29, 2016 (5 pages).
EP 13799858.9 Extended Search Report dated May 3, 2016 (13 pages).
EP 14856609.4 Extended European Search Report dated May 10, 2017 (9 pages).
EP 16783727.7 Extended European Search Report dated Sep. 11, 2018 (10 pages).
EP 16860818.0 Extended European Search Report dated Feb. 22, 2019 (11 pages).
PCT/US2011/032848 International Search Report dated Jan. 19, 2012 (4 pages).
PCT/US2011/032848 Written Opinion dated Jan. 19, 2012 (5 pages).
PCT/US2013/028888 International Search Report and Written Opinion dated Jul. 23, 2013 (13 pages).
PCT/US2013/044589 International Search Report and Written Opinion dated Nov. 13, 2013 (8 pages).
PCT/US2013/044592 International Search Report and Written Opinion dated Jan. 17, 2014 (12 pages).
PCT/US2013/044594 International Search Report and Written Opinion dated Nov. 13, 2013 (8 pages).
PCT/US2014/017367 International Search Report and Written Opinion dated Jun. 18, 2014 (8 pages).
PCT/US2014/061593 International Search Report dated Dec. 23, 2014 (6 pages).
PCT/US2014/061593 Written Opinion dated Dec. 23, 2014 (5 pages).
PCT/US2014/061624 International Search Report dated Dec. 23, 2014 (6 pages).
PCT/US2014/061624 Written Opinion dated Dec. 23, 2014 (5 pages).
PCT/US2014/061638 International Search Report and Written Opinion dated Feb. 20, 2015 (21 pages).
PCT/US2015/051402 International Search Report dated Oct. 5, 2016 (9 pages).
PCT/US2015/051402 Written Opinion dated Oct. 5, 2016 (8 pages).
PCT/US2015/051406 International Search Report dated Oct. 5, 2016 (12 pages).
PCT/US2015/051406 Written Opinion dated Oct. 5, 2016 (6 pages).
PCT/US2015/066683 International Search Report dated Oct. 5, 2016 (8 pages).
PCT/US2015/066683 Written Opinion dated Oct. 5, 2016 (8 pages).
PCT/US2016/028365 International Search Report and Written Opinion dated Dec. 8, 2016 (15 pages).
PCT/US2016/028368 International Search Report dated Oct. 5, 2016 (5 pages).
PCT/US2016/028368 Invitation to Pay Additional Fees dated Jul. 28, 2016 (2 pages).
PCT/US2016/028368 Written Opinion dated Oct. 5, 2016 (6 pages).
PCT/US2016/028562 International Search Report dated Jul. 29, 2016 (4 pages).
PCT/US2016/028562 Written Opinion dated Jul. 29, 2016 (5 pages).
PCT/US2016/059190 International Search Report and Written Opinion dated Jan. 19, 2017 (11 pages).
PCT/US2017/043383 International Search Report and Written Opinion dated Jan. 2, 2018 (13 pages).
PCT/US2017/044678 International Search Report and Written Opinion dated Oct. 24, 2017 (18 pages).
PCT/US2017/066417 International Search Report and Written Opinion dated Apr. 16, 2018 (19 pages).

\* cited by examiner

FIG. 1

CLUSTAL 2.1 multiple sequence alignment

```
human       MAEGEITTFETALTEKFNLPEGNYKKPKLLYCSNGGHFLRILPDGTVDGTRDRSDQHIQLQ 60
gorilla     MAEGEITTFETALTEKFNLPEGNYKKPKLLYCSNGGHFLRILPDGTVDGTRDRSDQHIQLQ 60
chimpanzee  MAEGEITTFTALTEKFNLPSGNYEKPKLLYCSNGGHFLRILPDGTVDGTRDRSDQHIQLQ 60
canine      MAEGEITTFETALTEKFNLPEGNYMKPKLLYCSNGGHFLRILPDGTVDGTRDRSDQHIQLQ 60
feline      MAEGEITTFETALTEKFNLPEGNYKKPKLLYCSNGGHFLRILPDGTVDGTRDRSDQHIQLQ 60
mouse       MAEGEITTFAALTERFNLPLGNYEKPKLLYCSNGGHFLRILPDGTVDGTRDRSDQHIQLQ 60
            ******:**:::****************************** human       LSAESVGEVYIKSTETGQYLAMDTDGLLYGSQTPNEECLFLERLEENHYNTYISKKHAEK 120
gorilla     LSAESVGEVYIKSTETGQYLAMDTDGLLYGSQTPNEECLFLERLEENHYNTYISKKHAEK 120
chimpanzee  LSAESVGEVYIKSTETGQYLAMDTDGLLYGSQTPNEECLFLERLEENHYNTYISKKHAEK 120
canine      LSAESVGEVYIKSTETGQYLAMDTDGLLYGSQTPNEECLFLERLEENHYNTYISKKHAEK 120
feline      LSAESVGEVYIKSTETGQYLAMDTDGLLYGSQTPNEECLFLERLEENHYNTWTYSKKHAEK 120
mouse       LSAESAGEVYIKGTETGQYLAMDTEGLLYGSQTPNEECLFLERLEENHYNTYTSKKHAEK 120
            ***:*.*******:*********************:: ::*** human       NWFVGLKKNGSCKRGPRTHYGQKAILFLPLPVSSD 155
gorilla     NWFVGLKKNGSCKRGPRTHYGQKAILFLPLPVSSD 155
chimpanzee  NWFVGLKKNGSCKRGPRTHYGQKAILFLPLPVSSD 155
canine      NWFVGLKKNGSCKRGPRTHYGQKAILFLPLPVSSD 155
feline      NWFVGLKKNGSCKRGPRTHYGQKAILFLPLPVSSD 155
mouse       NWFVGLKKNGSCKRGPRTHYGQKAILFLPLPVSSD 155
            **********************************
```

FIG. 2

SL001 FGF1(1-140αα)
N7H, N18D, D32E, Y64C, F85L, E90G, K101R, N114S

```
FNLPPGNYKK PKLLYCSNGG HFLRILPDGT VDGTRDRSDQ HIQLQLSAES VGEVYIKSTE TGQYLAMDTD
GLLYGSQTPN EECLFLERLE ENHYNTYISK KHAEKNWFVG LKKNGSCKRG PRTHYGQKAI LFLPLPVSSD
```

SL002 FGF1(1-140αα)
K10E, L13P, L44P, I96T, K113Q

```
FNLPPGNYKK PKLLYCSNGG HFLRILPDGT VDGTRDRSDQ HIQLQLSAES VGEVYIKSTE TGQYLAMDTD
GLLYGSQTPN EECLFLERLE ENHYNTYISK KHAEKNWFVG LKKNGSCKRG PRTHYGQKAI LFLPLPVSSD
```

SL003 FGF1(1-140αα)
N18D, G19R, K113E

```
FNLPPGNYKK PKLLYCSNGG HFLRILPDGT VDGTRDRSDQ HIQLQLSAES VGEVYIKSTE TGQYLAMDTD
GLLYGSQTPN EECLFLERLE ENHYNTYISK KHAEKNWFVG LKKNGSCKRG PRTHYGQKAI LFLPLPVSSD
```

SL004 FGF1(1-140αα)
S76P

```
FNLPPGNYKK PKLLYCSNGG HFLRILPDGT VDGTRDRSDQ HIQLQLSAES VGEVYIKSTE TGQYLAMDTD
GLLYGSQTPN EECLFLERLE ENHYNTYISK KHAEKNWFVG LKKNGSCKRG PRTHYGQKAI LFLPLPVSSD
```

SL001

SL002

SL003

SL004

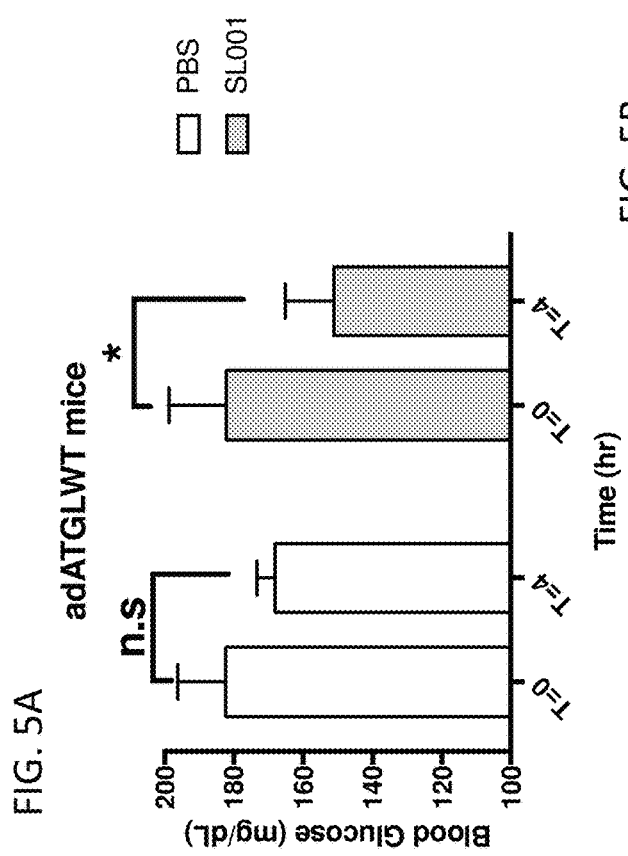
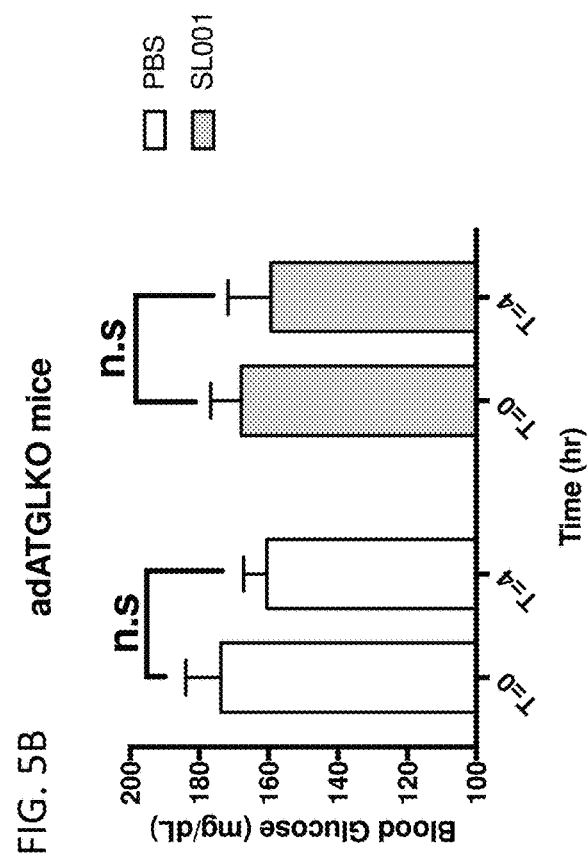
FIG. 5A
FIG. 5B

FIG. 9

ILKTAGVNTTDKEMEVLHLRNVSFEDAGEYTCLAGNSIGLSHHSAWLTVLE--ALEER   FGFR1c
ILKHSGINSSDAEVLTLF--NVTEAQSGEYVCKVSNYIGEANQSAWLTVTRPALEER   FGFR1b

FIBROBLAST GROWTH FACTOR 1 (FGF1) MUTANT PROTEINS THAT SELECTIVELY ACTIVATE FGFR1B TO REDUCE BLOOD GLUCOSE

CROSS REFERENCE TO RELATED APPLICATION

This application claims priority to U.S. Provisional Application No. 62/880,853 filed Jul. 31, 2019, herein incorporated by reference in its entirety.

FIELD

This application provides FGF1 mutant proteins that selectively bind FGFR1b, nucleic acids encoding such proteins, and their use for reducing blood glucose and/or treating a metabolic disease, for example in a diabetic patient.

BACKGROUND

Type 2 diabetes and obesity are leading causes of mortality and are associated with the Western lifestyle, which is characterized by excessive nutritional intake and lack of exercise. A central player in the pathophysiology of these diseases is the nuclear hormone receptor (NHR) PPARγ, a lipid sensor and master regulator of adipogenesis. PPARγ is also the molecular target for the thiazolidinedione (TZD)-class of insulin sensitizers, which command a large share of the current oral anti-diabetic drug market. However, there are numerous side effects associated with the use of TZDs such as weight gain, liver toxicity, upper respiratory tract infection, headache, back pain, hyperglycemia, fatigue, sinusitis, diarrhea, hypoglycemia, mild to moderate edema, and anemia. Thus, the identification of new insulin sensitizers is needed.

Glucagon-like peptide 1 (GLP-1) is secreted postprandially from intestinal L cells to stimulate the secretion of insulin from pancreatic β cells. In addition, GLP-1 improves the function of β cells. In vivo, GLP-1 is rapidly degraded by DPP-IV, limiting its half-life to minutes. Analogs of GLP-1, including those resistant to DPP-IV degradation such as exendin-4, are currently used to treat hyperglycemia in type 2 diabetic patients.

SUMMARY

Expression of the FGF receptor 1 (FGFR1) in adipose tissue is required for the glucose lowering effects of FGF1. It is shown herein that mutant FGF1 proteins that selectively activate the b splice variant of FGFR1 (FGFR1b) are sufficient to lower blood glucose levels in diabetic mammals in an insulin-dependent manner, and that FGFR1b signaling is less mitogenic than FGFR1c signaling. This ability to reduce blood glucose in vivo was dependent on expression of FGFR1b and adipose triglyceride lipase (ATGL in mice, PNPLA2 in humans) in adipose tissue, but not expression of insulin receptor (IR). Sustained levels of glucose lowering were achieved for at least 4 hours, and even up to 24 hours. The mutant FGF1 proteins that selectively bind FGFR1b and lowered blood glucose levels in diabetic mammals retained the ability to suppress HSL (lipe) expression following treatment with dexamethasone to induce insulin resistance.

Based on these observations, mutant FGF1 proteins (as well as nucleic acid molecules encoding such) are provided. Mutant FGF1 proteins can include an N-terminal truncation, one or more point mutation(s) (such as those in Table 1), or combinations thereof. In some examples, the FGF1 mutants have reduce mitogenic activity, altered heparan sulfate and/or heparin binding, and/or increased thermostability relative to a native FGF1 protein (e.g., SEQ ID NO: 4 or 5)). Specific FGF1 mutant proteins are provided in SEQ ID NOS: 10-13.

Methods of using the mutant FGF1 proteins, or nucleic acid molecules encoding such, for reducing blood glucose in a mammal, for example to treat a metabolic disease, are disclosed. Such FGF1 mutants can be used alone, in combination, or in combination with other agents, such as other glucose reducing agents, such as thiazolidinedione. In some examples, use of the disclosed mutant FGF1 proteins result in one or more of: reduction in triglycerides, decrease in insulin resistance, reduction of hyperinsulinemia, increase in glucose tolerance, or reduction of hyperglycemia in a mammal. In some examples, 1, 2, 3, 4 or 5 different FGF1 mutant proteins are used.

Provided herein are mutated FGF1 proteins containing an N-terminal truncation, one or more point mutation(s) (such as amino acid substitutions, deletions, additions, or combinations thereof), or combinations of N-terminal deletions and point mutation(s). In some examples, such the disclosed mutated FGF1 proteins have reduced mitogenicity relative to mature FGF1 (e.g., SEQ ID NO: 4 or 5), such as a reduction of at least 20%, at least 50%, at least 75%, at least 90%, or at least 95%. In some examples, mutated FGF1 proteins have increased thermostability relative to mature FGF1 (e.g., SEQ ID NO: 4 or 5), such as an increase of at least 20%, at least 50%, at least 75%, at least 90%, at least 100%, or at least 200%. In some examples, the disclosed mutated FGF1 proteins retain the ability to suppress HSL (lipe) expression, for example relative to mature FGF1 (e.g., SEQ ID NO: 4 or 5), for example following administration of dexamethasone to a mouse to induce insulin resistance. In some examples, the mutant FGF1 protein can include for example deletion of at least 5, at least 6, at least 10, at least 11, at least 12, at least 13, at least 14, at least 15, at least 16, at least 17, at least 18, at least 19, or at least 20 consecutive N-terminal amino acids, such as 3 to 14, 3 to 13, 3 to 12 N-terminal amino acids, or 9 N-terminal amino acids. In some examples, the deleted N-terminal amino acids are replaced with an amino acid sequence comprising or consisting of MRDSSPL, SYNHLQGDVR, SYNHLQGDVRV, or SYDYMEGGDIRV. In some examples, the mutant FGF1 protein includes point mutations, such as one containing at least 1, at least 2, at least 3, at least 4, at least 5, at least 6, at least 7, at least 8, at least 9, or at least 10 additional amino acid substitutions (such as 1, 2, 3, 4, 5, 6, 7, 8, 9, 10, 11, 12, 13, 14, 15, 16, 17, 18, or 19 substitutions), such as one or more conservative amino acid substitutions, and/or one or more of those shown in Table 1. In some examples, the mutant FGF1 protein includes both an N-terminal truncation and one or more additional point mutations (such as amino acid substitutions). In some examples, the mutant FGF1 protein includes at least 90, at least 100, or at least 110 consecutive amino acids from amino acids 5-141 of FGF1 (e.g., of SEQ ID NO: 2, 4 or 5), (which in some examples can include 1-20 point mutations, such as substitutions, deletions, and/or additions). In some examples, the mutated FGF1 protein has at least 80%, at least 85%, at least 90%, at least 95%, at least 96%, at least 97%, at least 99%, or 100% sequence identity to any one of SEQ ID NOS: 10, 11, 12, or 13, and retains the amino acid substitution shown herein.

Also provided are isolated nucleic acid molecules encoding the disclosed mutant FGF1 proteins. Vectors and cells that include such nucleic acid molecules are also provided.

Methods of using the disclosed mutant FGF1 proteins (or nucleic acid molecules encoding such) are provided. In some examples the methods include administering a therapeutically effective amount of one or more disclosed mutant FGF1 proteins (or nucleic acid molecules encoding such) to reduce blood glucose in a mammal, such as a decrease of at least 5%, at least 10%, at least 25%, at least 50%, or at least 75%. In some examples, the glucose lowering effect occurs within 4 hours, 6 hours, 8 hours, 12 hours, 18 hours, 20 hours, or 24 hours. In some examples, the glucose lowering effect lasts at least 4 hours, at least 6 hours, at least 8 hours, at least 12 hours, at least 18 hours, at least 20 hours, or at least 24 hours. In some examples the methods include administering a therapeutically effective amount of a disclosed mutant FGF1 protein (or nucleic acid molecules encoding such) to treat a metabolic disease in a mammal. Exemplary metabolic diseases that can be treated with the disclosed methods include, but are not limited to: diabetes (such as type 2 diabetes, non-type 2 diabetes, type 1 diabetes, latent autoimmune diabetes (LAD), or maturity onset diabetes of the young (MODY)), polycystic ovary syndrome (PCOS), metabolic syndrome (MetS), obesity, non-alcoholic steatohepatitis (NASH), non-alcoholic fatty liver disease (NAFLD), dyslipidemia (e.g., hyperlipidemia), and cardiovascular diseases (e.g., hypertension). In some examples, one or more of these diseases are treated simultaneously with the disclosed FGF1 mutant proteins. Also provided are methods of reducing fed and fasting blood glucose, improving insulin sensitivity and glucose tolerance, reducing systemic chronic inflammation, ameliorating hepatic steatosis in a mammal, or combinations thereof, by administering a therapeutically effective amount of a disclosed mutant FGF1 protein (or nucleic acid molecules encoding such).

The foregoing and other objects and features of the disclosure will become more apparent from the following detailed description, which proceeds with reference to the accompanying figures.

BRIEF DESCRIPTION OF THE DRAWINGS

FIG. 1 shows an alignment between different mammalian wild-type FGF1 sequences (human (SEQ ID NO: 2), gorilla (SEQ ID NO: 6), chimpanzee (SEQ ID NO: 7), canine (SEQ ID NO: 8), feline (SEQ ID NO: 8), and mouse (SEQ ID NO: 4)). Similar alignments can be generated and used to make the mutations provided herein to any FGF1 sequence of interest.

FIG. 2 shows four exemplary FGF1 mutant proteins (SEQ ID NOS: 10-13) that selectively bind FGFR1b. Substituted amino acids are highlighted.

FIGS. 5A-5B are graphs showing that the glucose lowering ability of FGF1 mutant SL001 (SEQ ID NO: 10) is dependent on adipose ATGL (adATGL) expression. (A) Blood glucose levels in wild type (adATGLWT) mice with moderate type 2 diabetes (T2D), before and 4 hours after treatment with PBS or SL001. (B) Blood glucose levels in adipose-specific ATGL knockout (adATGLKO) mice with T2D, before and 4 hours after treatment with PBS or SL001.

FIG. 9 shows an alignment of a portion of FGFR1c (SEQ ID NO: 18) and FGR1b (SEQ ID NO: 19) amino acid sequences.

SEQUENCE LISTING

Figure 3A:
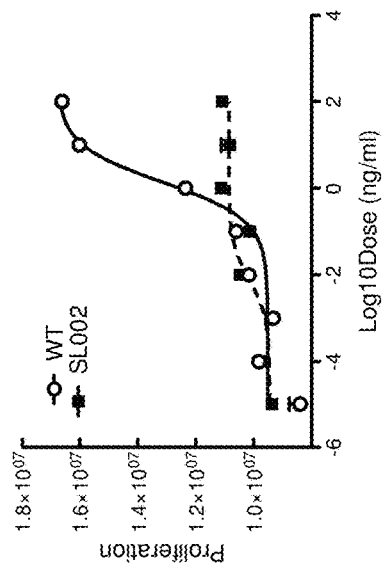
FIGS. 3A-3D are graphs showing that the FGF1 mutant proteins (A) SEQ ID NO: 10, (B) SEQ ID NO: 11, (C) SEQ ID NO: 12, and (D) SEQ ID NO: 13 have a reduced capacity to drive cell proliferation compared to wild type (WT) FGF1.
Figure 3B:
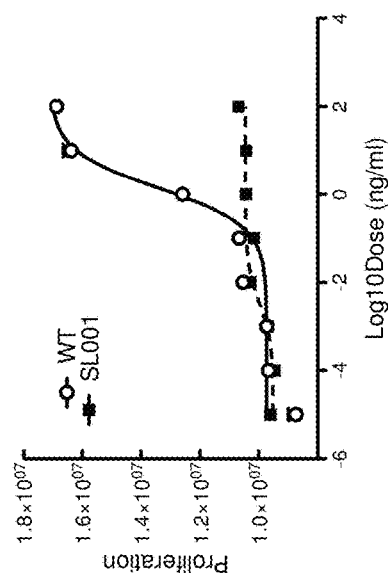
Figure 3C:
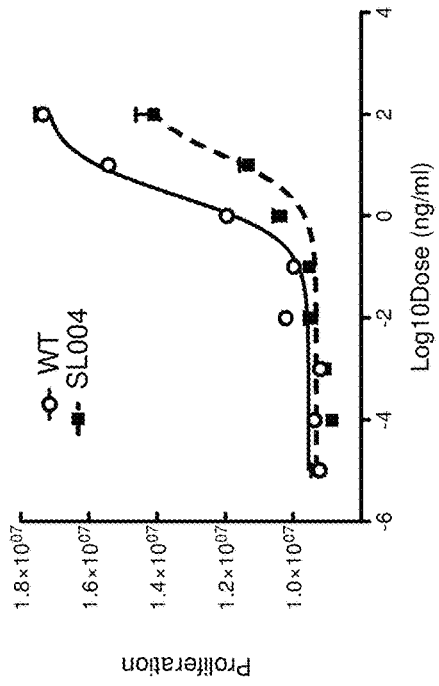
Figure 3D:
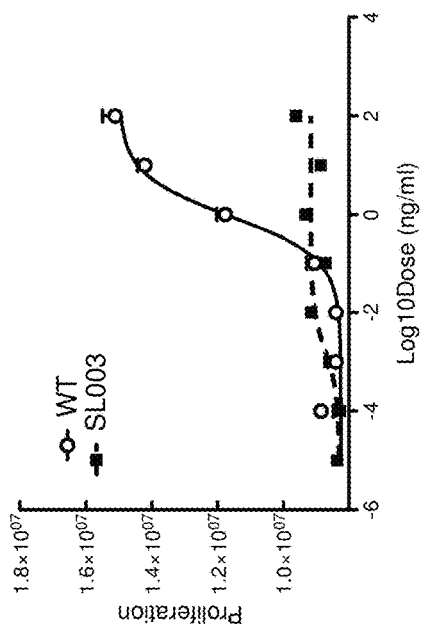

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The sequence listing filed herewith (generated on Jul. 4, 2020, 24 KB), is incorporated by reference in its entirety.

SEQ ID NOS: 1 and 2 provide an exemplary human FGF1 nucleic acid and protein sequences, respectively. Source: GenBank Accession Nos: BC032697.1 and AAH32697.1. Heparan binding residues are amino acids 127-129 and 133-134.

SEQ ID NOS: 3 and 4 provide an exemplary mouse FGF1 nucleic acid and protein sequences, respectively. Source: GenBank Accession Nos: BC037601.1 and AAH37601.1.

SEQ ID NO: 5 provides an exemplary mature form of human FGF1 (140 aa, sometimes referred to in the art as FGF1 15-154).

SEQ ID NO: 6 provides an exemplary gorilla FGF1 protein sequence.

SEQ ID NO: 7 provides an exemplary chimpanzee FGF1 protein sequence.

SEQ ID NO: 8 provides an exemplary dog FGF1 protein sequence.

SEQ ID NO: 9 provides an exemplary cat FGF1 protein sequence.

SEQ ID NO: 10 (SL001) provides an exemplary mature form of FGF1 with eight point mutations (N7H, N18D, D32E, Y64C, F85L, E90G, K101R, N114S) wherein numbering refers to SEQ ID NO: 5.

SEQ ID NO: 11 (SL002) provides an exemplary mature form of FGF1 with five point mutations (K10E, L13P, L44P, I98T, K113Q) wherein numbering refers to SEQ ID NO: 5.

SEQ ID NO: 12 (SL003) provides an exemplary mature form of FGF1 with three point mutations (N18D, G19R, K118E) wherein numbering refers to SEQ ID NO: 5.

SEQ ID NO: 13 (SL004) provides an exemplary mature form of FGF1 with a point mutation (S76P) wherein numbering refers to SEQ ID NO: 5.

SEQ ID NOS: 14-17 are exemplary peptides that target/bind FGF1Rb (MRDSSPL, SYNHLQGDVR, SYNHLQGDVRV, and SYDYMEGGDIRV, respectively). Each can replace an N-terminal sequence of a mutant FGF1 sequence provided herein (such as any of SEQ ID NOS: 10-13).

SEQ ID NO: 18 is a portion of an FGFR1c amino acid sequence.

SEQ ID NO: 19 is a portion of an FGFR1b amino acid sequence.

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a protein" includes single or plural proteins and is considered equivalent to the phrase "comprising at least one protein." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank® Accession Nos. referred to herein are the sequences available at least as early as Jul. 31, 2019. All references, including patents and patent applications, and GenBank® Accession numbers cited herein are incorporated by reference in their entireties.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided:

Administration: To provide or give a subject an agent, such as a mutated FGF1 protein, or nucleic acid molecule encoding such, by any effective route. Exemplary routes of administration include, but are not limited to, oral, injection (such as subcutaneous, intraosseous, intramuscular, intradermal, intraperitoneal, intravenous, intrathecal, and intratumoral), sublingual, rectal, transdermal, intranasal, vaginal and inhalation routes.

C-terminal portion: A region of a protein sequence that includes a contiguous stretch of amino acids that begins at or near the C-terminal residue of the protein. A C-terminal portion of the protein can be defined by a contiguous stretch of amino acids (e.g., a number of amino acid residues).

Diabetes mellitus: A group of metabolic diseases in which a subject has high blood sugar, either because the pancreas does not produce enough insulin, or because cells do not respond to the insulin that is produced. Type 1 diabetes results from the body's failure to produce insulin. This form has also been called "insulin-dependent diabetes mellitus" (IDDM) or "juvenile diabetes". Type 2 diabetes results from insulin resistance, a condition in which cells fail to use insulin properly, sometimes combined with an absolute insulin deficiency. This form is also called "non-insulin-dependent diabetes mellitus" (NIDDM) or "adult-onset diabetes." The defective responsiveness of body tissues to insulin is believed to involve the insulin receptor. Diabetes mellitus is characterized by recurrent or persistent hyperglycemia, and in some examples diagnosed by demonstrating any one of:

a. Fasting plasma glucose level≥7.0 mmol/l (126 mg/dl);
b. Plasma glucose≥11.1 mmol/l (200 mg/dL) two hours after a 75 g oral glucose load as in a glucose tolerance test;
c. Symptoms of hyperglycemia and casual plasma glucose≥11.1 mmol/l (200 mg/dl);
d. Glycated hemoglobin (Hb A1C)≥6.5%

Effective amount or therapeutically effective amount: The amount of agent, such as a mutated FGF1 protein (or nucleic acid molecules encoding such) disclosed herein, that is an amount sufficient to prevent, treat (including prophylaxis), reduce, and/or ameliorate the symptoms and/or underlying causes of any of a disorder or disease. In one embodiment, an "effective amount" is sufficient to reduce or eliminate a symptom of a disease, such as a diabetes (such as type II diabetes), for example by lowering blood glucose.

Fibroblast Growth Factor 1 (FGF1): e.g., OMIM 13220. Includes FGF1 nucleic acid molecules and proteins. FGF1 is a protein that binds to the FGF receptors and is also known as the acidic FGF. FGF1 sequences are publically available, for example from GenBank® sequence database (e.g., Accession Nos. NP_00791 and NP_034327 provide exemplary FGF1 protein sequences, while Accession Nos. NM_000800 and NM_010197 provide exemplary FGF1 nucleic acid sequences). One of ordinary skill in the art can identify additional FGF1 nucleic acid and protein sequences, including FGF1 variants.

Specific examples of native FGF1 sequences are provided in SEQ ID NOS: 1-9 and shown in FIG. 1. A native FGF1 sequence is one that does not include a mutation that alters the normal activity of the protein (e.g., activity of SEQ ID NOS: 2, 4 or 5-9). A mature FGF1 refers to an FGF1 peptide or protein product and/or sequence following any post-translational modifications (such as SEQ ID NO: 4 or 5). A mutated FGF1 is a variant of FGF1 with different or altered biological activity, such as reduced mitogenicity (e.g., a variant of any of SEQ ID NOS: 1-9, such as one having at least 90%, at least 95%, at least 96%, at least 97%, at least 98% or at least 99% sequence identity to any of SEQ ID NOS: 10-13, but is not a native/wild-type sequence, and in some examples retains the point mutation(s) noted herein for that sequence). In one example, such a variant includes an N-terminal truncation and/or one or more additional point muatations (such as one or more of those shown in Table 1), such as changes that decrease mitogenicity of FGF1, alter the heparin binding affinity of FGF1, and/or the thermostability of FGF1. Specific exemplary FGF1 mutant proteins are shown in SEQ ID NOS: 10-13.

Fibroblast Growth Factor Receptor 1b (FGFR1b): A member of the FGFR1 family found on the cell surface that has tyrosine kinase activity. The FGFR1 gene can be alternatively spliced to generate distinct mRNAs, which code for two FGFR1 isoforms: FGFR1b and FGFR1c (FIG. 9 shows an alignment of a portion of both sequences and their variations).

FGFR1b sequences are publically available, for example from GenBank® sequence database (e.g., Accession No. ACO38646.1 provides an exemplary FGFR1b protein sequence, while Accession No. FJ809917 provides an exemplary FGFR1b nucleic acid sequence). One of ordinary skill in the art can identify additional FGFR1b nucleic acid and protein sequences, including FGFR1b variants. In one example a human FGFR1b variant protein includes no amino acid substitution at I317, N318, E323, and/or Y345.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Thus, host cells can be transgenic, in that they include nucleic acid molecules that have been introduced into the cell, such as a nucleic acid molecule encoding a mutant FGF1 protein disclosed herein.

Isolated: An "isolated" biological component (such as a mutated FGF1 protein, or nucleic acid molecule encoding such) has been substantially separated, produced apart from, or purified away from other biological components in the cell of the organism in which the component naturally occurs, such as other chromosomal and extrachromosomal DNA and RNA, and proteins. Nucleic acid molecules and proteins which have been "isolated" thus include nucleic acids and proteins purified by standard purification methods. The term also embraces nucleic acid molecules and proteins prepared by recombinant expression in a host cell as well as chemically synthesized nucleic acids. A purified or isolated cell, protein, or nucleic acid molecule can be at least 70%, at least 80%, at least 90%, at least 95%, at least 96%, at least 97%, at least 98%, or at least 99% pure.

Mammal: This term includes both human and non-human mammals. Similarly, the term "subject" includes both human and veterinary subjects (such as cats, dogs, cows, and pigs) and rodents (such as mice and rats). In some examples, the mammal has or is a risk to develop type 2 diabetes or other metabolic disorder.

Metabolic disorder/disease: A disease or disorder that results from the disruption of the normal mammalian process of metabolism. For example, a metabolic disorder/disease includes metabolic syndrome.

Other examples include, but are not limited to, (1) glucose utilization disorders and the sequelae associated therewith, including diabetes mellitus (Type 1 and Type 2), gestational diabetes, hyperglycemia, insulin resistance, abnormal glucose metabolism, "pre-diabetes" (Impaired Fasting Glucose (IFG) or Impaired Glucose Tolerance (IGT)), and other physiological disorders associated with, or that result from, the hyperglycemic condition, including, for example, histopathological changes such as pancreatic β-cell destruction; (2) dyslipidemias and their sequelae such as, for example, atherosclerosis, coronary artery disease, cerebrovascular disorders and the like; (3) other conditions which may be associated with the metabolic syndrome, such as obesity and elevated body mass (including the co-morbid conditions thereof such as, but not limited to, nonalcoholic fatty liver disease (NAFLD), nonalcoholic steatohepatitis (NASH), and polycystic ovarian syndrome (PCOS)), and also include thrombosis, hypercoagulable and prothrombotic states (arterial and venous), hypertension, cardiovascular disease, stroke and heart failure; (4) disorders or conditions in which inflammatory reactions are involved, including atherosclerosis, chronic inflammatory bowel diseases (e.g., Crohn's disease and ulcerative colitis), asthma, lupus erythematosus, arthritis, or other inflammatory rheumatic disorders; (5) disorders of cell cycle or cell differentiation processes such as adipose cell tumors, lipomatous carcinomas including, for example, liposarcomas, solid tumors, and neoplasms; (6) neurodegenerative diseases and/or demyelinating disorders of the central and peripheral nervous systems and/or neurological diseases involving neuroinflammatory processes and/or other peripheral neuropathies, including Alzheimer's disease, multiple sclerosis, Parkinson's disease, progressive multifocal leukoencephalopathy, and Guillain-Barre syndrome; (7) skin and dermatological disorders and/or disorders of wound healing processes, including erythematosquamous dermatoses; and (8) other disorders such as syndrome X, osteoarthritis, and acute respiratory distress syndrome. Other examples are provided in WO 2014/085365 (herein incorporated by reference).

In specific examples, the metabolic disease includes one or more of (such as at least 2 or at least 3 of): diabetes (such as type 2 diabetes, non-type 2 diabetes, type 1 diabetes, latent autoimmune diabetes (LAD), or maturity onset diabetes of the young (MODY)), polycystic ovary syndrome (PCOS), metabolic syndrome (MetS), obesity, non-alcoholic steatohepatitis (NASH), non-alcoholic fatty liver disease (NAFLD), dyslipidemia (e.g., hyperlipidemia), and cardiovascular diseases (e.g., hypertension).

N-terminal portion: A region of a protein sequence that includes a contiguous stretch of amino acids that begins at or near the N-terminal residue of the protein. An N-terminal portion of the protein can be defined by a contiguous stretch of amino acids (e.g., a number of amino acid residues).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence (such as a mutated FGF1 coding sequence). Generally, operably linked DNA sequences are contiguous and, where necessary, join two protein coding regions, in the same reading frame.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15$^{th}$ Edition (1975), describes compositions and formulations suitable for pharmaceutical delivery of the disclosed mutated FGF1 proteins (or nucleic acid molecules encoding such) herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Recombinant: A recombinant nucleic acid molecule is one that has a sequence that is not naturally occurring (e.g., a mutated FGF1 protein) or has a sequence that is made by an artificial combination of two otherwise separated segments of sequence. This artificial combination can be accomplished by routine methods, such as chemical synthesis or by the artificial manipulation of isolated segments of nucleic acids, such as by genetic engineering techniques. Similarly, a recombinant protein is one encoded for by a recombinant nucleic acid molecule. Similarly, a recombinant or transgenic cell is one that contains a recombinant nucleic acid molecule and expresses a recombinant protein.

Sequence identity of amino acid sequences: The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn, and tblastx. A description of how to determine sequence identity using this program is available on the NCBI website on the internet.

Variants of the mutated FGF1 proteins and coding sequences disclosed herein, are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Thus, a mutant FGF1 protein provided herein, can share at least 80%, at least 85%, at least 90%, at least 91%, at least 92%, at least 95%, at least 96%, at least 97%, at least 98% or at least 99% sequence identity to any one of SEQ ID NOS: 10-13 (such as to SEQ ID NO: 10, 11, 12, or 13), but is not SEQ ID NOS: 2, 4, or 5 (which, in some examples, has the point mutation(s) recited herein for that sequence, such as one or more, such as 1, 2, 3, 4, 5, 6, 7, 8, 9, 1, 11, 12, 131, 14, 15, 16, or 17 of the mutations shown in Table 1). In addition, exemplary mutated FGF1 proteins have at least 80%, at least 85%, at least 90%, at least 92%, at least 95%, at least 96%, at least 97%, at least 98% or at least 99% sequence identity to any one of SEQ ID NOS: 10-13 (such as to SEQ ID NO: 10, 11, 12, or 13), and retain the ability to reduce blood glucose levels in vivo.

Subject: Any mammal, such as humans, non-human primates, pigs, sheep, cows, dogs, cats, rodents and the like which is to be the recipient of the particular treatment, such as treatment with a mutated FGF1 protein (or corresponding nucleic acid molecule) provided herein. In two non-limiting examples, a subject is a human subject or a murine subject. In some examples, the subject has one or more metabolic diseases, such as diabetes (e.g., type 2 diabetes, non-type 2 diabetes, type 1 diabetes, latent autoimmune diabetes (LAD), or maturity onset diabetes of the young (MODY)), polycystic ovary syndrome (PCOS), metabolic syndrome (MetS), obesity, non-alcoholic steatohepatitis (NASH), non-alcoholic fatty liver disease (NAFLD), dyslipidemia (e.g., hyperlipidemia), cardiovascular disease (e.g., hypertension), or combinations thereof. In some examples, the subject has elevated blood glucose.

Transduced and Transformed: A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

Exemplary methods of transfection include chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses (Wolff, J. A., ed., Gene Therapeutics, Birkhauser, Boston, USA (1994)). In the case of infection by retroviruses, the infecting retrovirus particles are absorbed by the target cells, resulting in reverse transcription of the retroviral RNA genome and integration of the resulting provirus into the cellular DNA.

Transgene: An exogenous gene supplied by a vector. In one example, a transgene includes a mutated FGF1 coding sequence.

Vector: A nucleic acid molecule as introduced into a host cell, thereby producing a transformed host cell. A vector may include nucleic acid sequences that permit it to replicate in the host cell, such as an origin of replication. A vector may also include one or more mutated FGF1 coding sequences, and/or selectable marker genes and other genetic elements. A vector can transduce, transform, or infect a cell, thereby causing the cell to express nucleic acids and/or proteins other than those native to the cell. A vector optionally includes materials to aid in achieving entry of the nucleic acid into the cell, such as a viral particle, liposome, protein coating, or the like.

Overview

Provided herein are mutated FGF1 proteins, which can include an N-terminal deletion, one or more additional point mutations (such as amino acid substitutions, deletions, additions, or combinations thereof), or combinations of an N-terminal deletion and an additional one or more point mutations. The disclosed mutated FGF1 proteins have specificity for the b splice variant of FGFR1. For example, the disclosed mutated FGF1 proteins have a greater binding affinity for the b splice variant of FGFR1 than the c splice variant of FGFR1, and selectively activate FGFR1b.

Also provided are methods of using the disclosed FGF1 mutant proteins (or their nucleic acid coding sequences) to lower glucose, for example to treat one or more metabolic diseases, or combinations thereof. Exemplary metabolic diseases that can be treated with the disclosed methods include, but are not limited to: type 2 diabetes, non-type 2 diabetes, type 1 diabetes, polycystic ovary syndrome (PCOS), metabolic syndrome (MetS), obesity, non-alcoholic steatohepatitis (NASH), non-alcoholic fatty liver disease (NAFLD), dyslipidemia (e.g., hyperlipidemia), cardiovascular diseases (e.g., hypertension), latent autoimmune diabetes (LAD), or maturity onset diabetes of the young (MODY).

In some examples, an FGF1 mutant protein has at least 80%, at least 85%, at least 90%, at least 92%, at least 95%, at least 96%, at least 97%, at least 98%, at least 99%, or 100% sequence identity to SEQ ID NO: 10, 11, 12, or 13. In some examples, an FGF1 mutant protein having at least 80%, at least 85%, at least 90%, at least 92%, at least 95%, at least 96%, at least 97%, at least 98%, at least 99% sequence identity to SEQ ID NO: 10, 11, 12, or 13 retains the point mutation(s) described herein for that sequence. In one example, an FGF1 mutant protein having at least 80%, at least 85%, at least 90%, at least 92%, at least 95%, at least 96%, at least 97%, at least 98%, at least 99% sequence identity to SEQ ID NO: 10 retains the N7H, N18D, D32E, Y64C, F85L, E90G, K101R, N114S substitutions. In one example, an FGF1 mutant protein having at least 80%, at least 85%, at least 90%, at least 92%, at least 95%, at least 96%, at least 97%, at least 98%, at least 99% sequence identity to SEQ ID NO:11 can retain the K10E, L13P, L44P, I98T, and K113Q substitutions. In one example, an FGF1 mutant protein having at least 80%, at least 85%, at least 90%, at least 92%, at least 95%, at least 96%, at least 97%, at least 98%, at least 99% sequence identity to SEQ ID NO:12 can retain the N1D, G19R, and K118E substitutions. In one example, an FGF1 mutant protein having at least 80%, at least 85%, at least 90%, at least 92%, at least 95%, at least 96%, at least 97%, at least 98%, at least 99% sequence identity to SEQ ID NO:13 can retain the S76P substitution. In some examples, the FGF1 mutant protein includes or consists of any of one SEQ ID NOS: 10, 11, 12, or 13. The disclosure encompasses variants of the disclosed FGF1 mutant proteins, such as any of one SEQ ID NOS: 10, 11, 12, or 13 having 1 to 8, 2 to 10, 1 to 5, 1 to 6, or 5 to 10 additional mutations, such as conservative amino acid substitutions.

In some examples, the mutant FGF1 protein includes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 or at least 25 amino acid substitutions, such as 1-20, 1-10, 4-8, 5-25, 1-5, 1-6, 1-7, 1-8, 2-5, 2-7, 1, 2, 3, 4, 5, 6, 7, 8, 9, 10, 11, 12, 13, 14, 15, 16, 17, 18, 19, 20, 21, 22, 23, 24, or 25 amino acid substitutions (such as those shown in Table 1). In some examples, the mutant FGF1 protein further includes deletion of one or more amino acids, such as deletion of 1-10, 4-8, 5-10, 1, 2, 3, 4, 5, 6, 7, 8, 9, 10, 11, 12, 13, 14, 15, 16, 17, 18, 19, or 20 amino acid deletions. In some examples, the mutant FGF1 protein includes a combination of amino acid substitutions and deletions, such as at least 1 substitution and at least 1 deletion, such as 1 to 10 substitutions with 1 to 10 deletions.

TABLE 1

Exemplary FGF1 mutations

| Location of Point Mutation Position in SEQ ID NO: 2 | Mutation Citation | Location of Point Mutation Position in SEQ ID NO: 5 |
|---|---|---|
| N22 | N7H | N7 |
| K25 | K10E | K10 |
| L28 | L13P | L13 |
| N33 | N18D | N18 |
| G34 | G19R | G19 |
| D47 | D32E | D32 |
| L59 | L44P | L44 |
| Y79 | Y64C | Y64 |
| S91 | S76P | S76 |
| F100 | F85L | F85 |
| E105 | E90G | E90 |
| I113 | I98T | I98 |
| K116 | K101R | K101 |
| K128 | K113Q | K113 |
| N129 | N114S | N114 |
| K133 | K118E | K118 |

Exemplary mutations that can be made to a mutant FGF1 protein are shown in Table 1, with amino acids referenced to either SEQ ID NOS: 2 or 5. One skilled in the art will recognize that these mutations can be used singly, or in any combination (such as 1-17, 1-10, 1-3, 1-5, 1-8, 2-8, 4-8, such as 1, 2, 3, 4, 5, 6, 7, 8, 9, 10, 11, 12, 13, 14, 15, 16 or 17 of these amino acid substitutions and/or deletions).

In some examples, the mutant FGF1 protein includes mutations at one or more of the following positions: N7, K10, L13, N18, G19, D32, L44, Y64, S76, F85, E90, I98, K101, K113, N114, and K118, such as 1 to 3, 1 to 5, 1 to 6, 1 to 7, 1 to 8, 2 to 5, 3 to 5, 3 to 6, 3 to 8, 1, 2, 3, 4, 5, 6, 7, 8, 9, 10, 11, 12, 13, 14, 15, 16, or 17 of these positions (wherein the position refers to SEQ ID NO: 5).

In some examples, the mutant FGF1 protein includes at least 90 consecutive amino acids from amino acids 5-141 of FGF1 (e.g., of SEQ ID NOS: 2 or 4), (which in some examples can include further deletion of N-terminal amino acids (such as deletion of up to 9, 10, 11, or 12 N-terminal amino acids) and/or 1 to 20 further point mutations, such as substitutions, deletions, and/or additions). In some examples, the mutant FGF1 protein includes at least 100 or at least 110 consecutive amino acids from amino acids 5-141 of FGF1, such as at least 100 consecutive amino acids from amino acids 5-141 of SEQ ID NO: 2 or 4 or at least 100 consecutive amino acids from SEQ ID NO: 5. In some examples, the mutant FGF1 protein includes at least 50, at least 75, at least 100 or at least 110 consecutive amino acids from SEQ ID NO: 10, 11, 12, or 13.

In some examples, the mutant FGF1 protein includes both an N-terminal truncation and additional point mutations. Specific exemplary FGF1 mutant proteins are shown in SEQ ID NO: 10, 11, 12, and 13. In some examples, the FGF1 mutant protein includes an N-terminal deletion (such as deletion of up to 9, 10, 11, or 12 N-terminal amino acids), but includes a methionine at its N-terminus. In some examples, the FGF1 mutant protein is 100-140, 100-130, 100-125, 100-120, 120-140, 125-140, or 130-140 amino acids in length. Thus, in some examples, SEQ ID NO: 10, 11, 12, or 13 is truncated at its N-terminus and includes additional internal amino acid deletions.

Also provided are isolated nucleic acid molecules encoding the disclosed mutated FGF1 proteins, such as a nucleic acid molecule encoding a protein having at least 80%, at least 85%, at least 90%, at least 95%, at least 98%, or at least 99% sequence identity to any of one SEQ ID NOS: 10, 11, 12, or 13. Vectors and cells that include such nucleic acid molecules are also provided. For example, such nucleic acid molecules can be expressed in a host cell, such as a bacterium or yeast cell (e.g., *E. coli*), thereby permitting expression of the mutated FGF1 protein. The resulting protein can be purified from the cell.

Methods of using the disclosed mutated FGF1 proteins are provided. Such methods include administering a therapeutically effective amount of at least one disclosed mutated FGF1 protein (such as at least 0.01 mg/kg, at least 0.05 mg/kg, at least 0.1 mg/kg, or at least 0.5 mg/kg) (or nucleic acid molecules encoding such) (such as 2, 3, or 4 disclosed mutated FGF1 proteins, or other FGF1 mutant proteins) to reduce blood glucose in a mammal, such as a decrease of at least 5%, at least 10%, at least 25% or at least 50%, for example as compared to administration of no mutant FGF1 mutant protein (e.g., administration of PBS).

In one example, the method is a method of reducing fed and fasting blood glucose, improving insulin sensitivity and glucose tolerance, reducing systemic chronic inflammation, ameliorating hepatic steatosis in a mammal, reducing triglycerides, decreasing insulin resistance, reducing hyperinsulinemia, increasing glucose tolerance, reducing hyperglycemia, or combinations thereof. Such a method can include administering a therapeutically effective amount of one or more disclosed mutated FGF1 proteins (such as at least 0.01 mg/kg, at least 0.05 mg/kg, at least 0.1 mg/kg, or at least 0.5 mg/kg), or nucleic acid molecules encoding such proteins, to reduce fed and fasting blood glucose, improve insulin sensitivity and glucose tolerance, reduce systemic chronic inflammation, ameliorate hepatic steatosis in a mammal, or combinations thereof.

In one example, the method is a method of treating a metabolic disease (such as metabolic syndrome, diabetes, or obesity) in a mammal. Such a method can include administering a therapeutically effective amount of one or more disclosed mutated FGF1 proteins (such as at least 0.01 mg/kg, at least 0.05 mg/kg, at least 0.1 mg/kg, or at least 0.5 mg/kg), or nucleic acid molecules encoding such proteins, to treat the metabolic disease.

In some examples, the mammal, such as a human, cat, or dog, has diabetes. Methods of administration are routine, and can include subcutaneous, intraperitoneal, intramuscular, or intravenous injection or infusion. In some examples, the mutated FGF1 protein is a mutated canine FGF1 protein, and is used to treat a dog. For example, a canine FGF1 (such as XP_849274.1) can be mutated to include one or more of the mutations disclosed herein (such as the combinations shown in SEQ ID NO: 10, 11, 12, or 13). Similarly, in some embodiments, the mutated FGF1 protein is a mutated cat FGF1 protein, and is used to treat a cat. Thus, for example, a feline FGF1 (such as XP_011281008.1) can be mutated to include one or more of the mutations disclosed herein (such as the combinations shown in SEQ ID NO: 10, 11, 12, or 13). Based on routine methods of sequence alignment (e.g., see FIG. 1), one skilled in the art can mutate any known FGF1 sequence to generate mutations that correspond to those provided herein (for example, the FGF1 sequence can be selected based on the subject to be treated, e.g., a dog can be treated with a mutated canine FGF1 protein or corresponding nucleic acid molecule).

In some examples, use of the FGF1 mutants disclosed herein does not lead to (or significantly reduces, such as a reduction of at least 20%, at least 50%, at least 75%, or at least 90%) the adverse side effects observed with thiazolidinediones (TZDs) therapeutic insulin sensitizers, including weight gain, increased liver steatosis and bone fractures (e.g., reduced effects on bone mineral density, trabecular bone architecture and cortical bone thickness).

Provided are methods of reducing fed and fasting blood glucose, improving insulin sensitivity and glucose tolerance, reducing systemic chronic inflammation, ameliorating hepatic steatosis, or combinations thereof, in a mammal, such as within 4 hours, within 6 hours, or within 24 hours of the treatment, such as within 4 to 24 hours, within 4 to 8 hours, or within 4 to 12 hours. In some examples, such treatment reduces blood glucose for at least 2 hours, at least 4 hours, at least 12 hours, at least 18 hours, at least 24 hours, or longer. Such methods can include administering a therapeutically effective amount of a FGF1 mutant disclosed herein, to the mammal, or a nucleic acid molecule encoding the FGF1 mutant or a vector comprising the nucleic acid molecule, thereby reducing fed and fasting blood glucose, improving insulin sensitivity and glucose tolerance, reducing systemic chronic inflammation, ameliorating hepatic steatosis, reducing one or more non-HDL lipid levels, or combinations thereof, in a mammal. In some examples, the fed and fasting blood glucose is reduced in the treated subject by at least 10%, at least 20%, at least 30%, at least 50%, at least 75%, or at least 90% as compared to an absence of administration of the FGF1 mutant. In some examples, insulin sensitivity and glucose tolerance is increased in the treated subject by at least 10%, at least 20%, at least 30%, at least 50%, at least 75%, or at least 90% as compared to an absence of administration of the FGF1 mutant. In some examples, systemic chronic inflammation is reduced in the treated subject by at least 10%, at least 20%, at least 30%, at least 50%, at least 75%, or at least 90% as compared to an absence of administration of the FGF1 mutant. In some examples, hepatic steatosis is reduced in the treated subject by at least 10%, at least 20%, at least 30%, at least 50%, at least 75%, or at least 90% as compared to an absence of administration of the FGF1 mutant. In some examples, one or more lipids (such as a non-HDL, for example IDL, LDL and/or VLDL) are reduced in the treated subject by at least 10%, at least 20%, at least 30%, at least 50%, at least 75%, or at least 90% as compared to an absence of administration of the FGF1 mutant. In some examples, triglyceride and or cholesterol levels are reduced with the FGF1 mutant by at least 10%, at least 20%, at least 30%, at least 50%, at least 75%, or at least 90% as compared to an absence of administration of the FGF1 mutant. In some examples, combinations of these reductions are achieved.

Mutated FGF1 Proteins

The present disclosure provides mutated FGF1 proteins. FGF1 mutants include those FGF1 protein sequences that vary from a native FGF1 sequence (such as any of SEQ ID NOS: 1-9), for example include an N-terminal deletion, one or more point mutations (such as amino acid substitutions, deletions, additions, or combinations thereof), or combinations of N-terminal deletions and one or more additional point mutations. The disclosed mutated FGF1 proteins, and corresponding coding sequences, can be used in the methods provided herein.

FGF1

FGF1 (such as SEQ ID NOS: 2, 4, 5, 6, 7, 8, or 9) can be mutated to include mutations to control (e.g., reduce) the mitogenicity of the protein and to provide glucose-lowering ability to the protein. Mutations can also be introduced to affect the stability and receptor binding selectivity of the protein.

FIG. 1 shows an alignment between different mammalian wild-type FGF1 sequences: human (SEQ ID NO: 2), gorilla (SEQ ID NO: 6), chimpanzee (SEQ ID NO: 7), canine (SEQ ID NO: 8), feline (SEQ ID NO: 8), and mouse (SEQ ID NO: 4). In some examples, FGF1 includes SEQ ID NO: 2, 4, 6, 7 or 8, but without the N-terminal methionine (resulting in a 154 aa FGF1 protein). In addition, the mature/active form of FGF1 is one where a portion of the N-terminus is removed, such as the N-terminal 15, 16, 20, or 21 amino acids from SEQ ID NO: 2, 4, 6, 7 or 8. Thus, in some examples the active form of FGF1 comprises or consists of amino acids 16-155 or 22-155 of SEQ ID NOS: 2 or 4 (e.g., see SEQ ID NO: 5). In some examples, the mature form of FGF1 that can be mutated includes SEQ ID NO: 5 with a methionine added to the N-terminus (wherein such a sequence can be mutated as discussed herein). Thus, a mutated mature FGF1 protein can include an N-terminal truncation.

In some examples, multiple types of mutations disclosed herein are made to an FGF1 protein. Although mutations below are noted by a particular amino acid for example in SEQ ID NOS: 2, 4, or 5, one skilled in the art will appreciate that the corresponding amino acid can be mutated in any FGF1 sequence (for example by using the alignment shown in FIG. 1, or by generating a similar alignment for the FGF1 of interest). For example, Q40 of SEQ ID NO: 5 corresponds to Q55 of SEQ ID NOS: 2 and 4.

In some examples, the mutant FGF1 is a truncated version of the mature protein (e.g., SEQ ID NO: 5), which can include for example deletion of at least 5, at least 6, at least 9, at least 10, at least 11, or at least 12 consecutive N-terminal amino acids. Thus, in some examples, the mutant FGF1 protein is a truncated version of the mature protein (e.g., SEQ ID NO: 5), such a deletion of the N-terminal 5, 6, 7, 8, 9, 10, 11, or 12 amino acids shown in SEQ ID NO: 5. For example, mutations can be made to the N-terminal region of FGF1 (such as SEQ ID NOS: 2, 4, or 5), such as deletion of the first 14, 15, 16, 17, 18, 19, 20, 21, 22, 23, 24, 25, 26, or 27 amino acids of SEQ ID NOS: 2 or 4 (such as deletion of at least the first 14 amino acids of SEQ ID NO: 2 or 4, such as deletion of at least the first 15, at least 16, at least 20, at least 25, or at least 27 amino acids of SEQ ID NOS: 2 or 4), deletion of the first 8, 9, 10, 11, or 12 amino acids of SEQ ID NO: 5. In some examples, the FGF1 mutant includes an N-terminal deletion, but has a methionine at the N-terminal position. In some examples, a mutant FGF1 protein has reduced mitogenic activity as compared to wild-type mature FGF1 protein. In some examples, an N-terminally deleted FGF1 protein has amino acids added back to the N-terminus, such as adding the sequence MRDSSPL (referred to as NF21) or a sequence that binds FGF1Rb (e.g., SYNHLQGDVR, SYNHLQGDVRV, or SYDYMEGGDIRV) to the N-terminus. In some examples, an N-terminally deleted FGF1 protein has reduced mitogenic activity as compared to wild-type mature FGF1 protein (e.g., SEQ ID NOS: 2, 4-9).

Thus, in some examples, the mutant FGF1 protein includes at least 90 consecutive amino acids from amino acids 5-141 or 5-155 of FGF1 (e.g., of SEQ ID NOS: 2 or 4), (which in some examples can include further deletion of up to 9, 10, 11 or 12 N-terminal amino acids and/or point mutations, such as substitutions, deletions, and/or additions). In some examples, the mutant FGF1 protein includes at least 90 consecutive amino acids from amino acids 1-140 of FGF1 (e.g., of SEQ ID NO: 5), (which in some examples can include further deletion of up to 9, 10, 11 or 12 N-terminal amino acids, alone or in combination with 1 to 20 point mutations, such as substitutions, deletions, and/or additions). Thus, in some examples, the mutant FGF1 protein includes at least 90 consecutive amino acids from amino acids 5-141 of FGF1, such as at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 115, at least 120, at least 125, or at least 130 consecutive amino acids from amino acids 5-141 of SEQ ID NOS: 2 or 4 (such as 90-115, 90-125, 90-100, or 90-95 consecutive amino acids from amino acids 5-141 of SEQ ID NOS: 2 or 4). In some examples, the mutant FGF1 protein includes least 90 consecutive amino acids from SEQ ID NO: 5. Thus, in some examples, the mutant FGF1 protein includes at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, or at least 110 consecutive amino acids from SEQ ID NO: 5 (such as 90-115, 90-100, or 90-95 consecutive amino acids from SEQ ID NO: 5). In some examples, the mutant FGF1 protein includes at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, or at least 110 consecutive amino acids from SEQ ID NO: 10, 11, 12, or 13 (such as 90-115, 90-100, or 90-95 consecutive amino acids from SEQ ID NO: 10, 11, 12, or 13).

In some examples, the mutant FGF1 protein (such as SEQ ID NO: 10, 11, 12, or 13) includes at least 1, at least 4, at least 5, at least 6, at least 7, at least 8, at least 9, at least 10, at least 11, at least 12, at least 13, at least 14, at least 15, at least 16, at least 17, at least 18, at least 19, or at least 20 additional amino acid substitutions (e.g., in addition to the amino acid substitutions provided in SEQ ID NO: 10, 11, 12, or 13), such as 1-20, 1-10, 4-8, 5-12, 5-10, 5-25, 1, 2, 3, 4, 5, 6, 7, 8, 9, 10, 11, 12, 13, 14, or 15 additional amino acid substitutions. For example, point mutations can be introduced into an FGF1 sequence to decrease mitogenicity, increase stability, alter binding affinity for heparin and/or heparan sulfate (compared to the portion of a native FGF1 protein without the modification), or combinations thereof. Specific exemplary point mutations that can be used are shown above in Table 1.

In some examples, the mutant FGF1 protein includes one or more mutations (such as a substitution or deletion) at one or more of the following positions: N7, K10, L13, N18, G19, D32, L44, Y64, S76, F85, E90, I98, K101, K113, N114, and K118, such as 1, 2, 3, 4, 5, 6, 7, 8, 9, 10, 11, 12, 13, 14, 15, or 16, of these positions. In some examples the mutant FGF1 protein has as one or more of N7H, K10E, L13P, N18D, G19R, D32E, L44P, Y64C, S76P, F85L, E90G, I98T, K101R, K113Q, N114S, and K118E (wherein the numbering refers to SEQ ID NO: 5), such as 1 to 3, 1 to 4, 1 to 5, 1 to 6, 1 to 7, 1 to 8, 1 to 10, 2 to 5, 2 to 10, 3 to 6, or 2 to 8 of these mutations, such as 1, 2, 3, 4, 5, 6, 7, 8, 9, 10, 11, 12, 13, 14, 15, or 16 of these mutations.

Mutant FGF1 proteins can include both an N-terminal deletion and one or more point mutations, such as those shown in Table 1. Thus, any of SEQ ID NOS: 10, 11, 12, or 13 can be modified to include one or more of the point mutations shown in Table 1.

Specific exemplary FGF1 mutant proteins are shown in SEQ ID NOS: 10, 11, 12, and 13. One skilled in the art will recognize that variations can be made to these sequences, without adversely affecting the function of the protein (such as its ability to reduce blood glucose and have reduced mitogenicity). In some examples, an FGF1 mutant protein includes at least 80% sequence identity to SEQ ID NO: 10, 11, 12, or 13, such as at least 80% sequence identity to SEQ ID NO: 10, 11, 12, or 13. Thus, a FGF1 mutant protein can have at least 85%, at least 90%, at least 95%, at least 96%, at least 97%, at least 98% or at least 99% sequence identity to SEQ ID NO: 10, 11, 12, or 13, and retains the ability to treat a metabolic disease and/or decrease blood glucose in a mammal (such as a mammal with type II diabetes), and in some example retains the point mutation(s) noted herein for each particular SEQ ID NO. However, such variants are not a native FGF1 sequence, e.g., SEQ ID NOS: 2, 4-9. In some examples, the FGF1 mutant protein includes or consists of SEQ ID NO: 10, 11, 12, or 13. The disclosure encompasses variants of the disclosed FGF1 mutant proteins, such as variants of SEQ ID NO: 10, 11, 12, or 13, having 1 to 50, 1 to 40, 1 to 30, 1 to 25, 1 to 20, 1 to 15, 1 to 10, 1 to 8, 2 to 10, 1 to 5, 1 to 6, 2 to 12, 3 to 12, 5 to 12, 5 to 50, 10 to 50, 10 to 20, or 5 to 10 additional mutations, such as conservative amino acid substitutions.

In some examples, the mutant FGF1 protein has at its N-terminus a methionine. In some examples, the mutant FGF1 protein is at least 90 amino acids in length, such as at least 100, at least 110, at least 120, at least 125, at least 130, at least 135, at least 140, at least 145, at least 150, at least 155, at least 160, or at least 175 amino acids in length, such as 90-140, 90-130, 100-120, 90-120, 90-110, 120-160, 125-160, 130-160, 150-160, 130-200, 130-180, 130-170, or 120-160 amino acids in length.

In some examples, the disclosed FGF1 mutant proteins have reduced mitogenicity compared to mature native FGF1 (e.g., SEQ ID NO: 5), such as a reduction of at least 20%, at least 50%, at least 75% or at least 90%.

In one example, the disclosed FGF1 mutant proteins have improved thermostability compared to mature native FGF1 (e.g., SEQ ID NO: 5), such as an increase of at least 10%, at least 20%, at least 50%, or at least 75% (e.g., see Xia et al., *PLoS One*. 2012; 7(11):e48210 and Zakrzewska, *J Biol Chem*. 284:25388-25403, 2009). Exemplary methods of measuring FGF1 stability include measuring denaturation of FGF1 or mutants by fluorescence and circular dichroism in the absence and presence of a 5-fold molar excess of heparin in the presence of 1.5 M urea or isothermal equilibrium denaturation by guanidine hydrochloride. In one example, the assay provided by Dubey et al., *J. Mol. Biol.* 371:256-268, 2007 is used to measure FGF1 stability.

In one example, the disclosed FGF1 mutant proteins have improved protease resistance compared to mature native FGF1 (e.g., SEQ ID NO: 5), such as an increase of at least 10%, at least 20%, at least 50%, or at least 75% (e.g., see Kobielak et al., *Protein Pept Lett.* 21(5):434-43, 2014).

In some examples, an FGF1 mutant protein has increased blood glucose lowering ability relative to the mature wild-type FGF1 (e.g., SEQ ID NO: 5), such as an increase of at least 10%, at least 20%, at least 50%, at least 75%, or at least 90%. In some examples, the FGF1 mutant protein has a similar glucose lowering to mature wild-type FGF1 (e.g., SEQ ID NO: 5). Methods of measuring blood glucose are known and are provided herein. In one example, blood (e.g., serum) is collected and glucose measured using a glucose meter or enzyme linked immunosorbent assay (ELISA). In some examples blood glucose is measured after fasting. In some examples, glucose tolerance tests (GTT) are conducted, for example after fasting. In some examples, pyruvate tolerance test (PTT) are conducted, for example after fasting.

In some examples, a mutated FGF1 includes one or more mutations that increase the thermostability (e.g., relative to mature or truncated FGF1, e.g., SEQ ID NO: 5), such as an increase of at least 20%, at least 50%, at least 75% or at least 90% compared to native FGF1. For example, a mutated FGF1 can be mutated to increase the thermostability of the protein relative to an FGF1 protein without the modification. Methods of measuring thermostability are known in the art. In one example, the method provided in Xia et al., PloS One. 7:e48210, 2012 is used.

A mutant FGF1 (such as SEQ ID NO: 10, 11, 12, or 13) can have reduced mitogenic activity (e.g., relative to the mature wild-type FGF1, e.g., SEQ ID NO: 5). In some examples, such mutants have reduced mitogenic activity, such as a reduction of at least 20%, at least 50%, at least 60%, at least 70%, at least 75%, at least 80%, at least 90%, at least 92%, at least 95%, at least 98%, at least 99%, or even complete elimination of detectable mitogenic activity, as compared to a native FGF1 protein without the mutation. In some examples, the FGF1 mutant protein has an $EC_{50}$ for mitogenicity that is shifted by several orders of magnitude relative to the mature wild-type FGF1 (e.g., SEQ ID NO: 5) (such as an $EC_{50}$ increase of 1 log, 2 logs, or 3 logs), or even no detectable mitogenicity. Methods of measuring mitogenicity are known and are provided herein. Examples include thymidine incorporation into DNA in serum-starved cells (e.g., NIH 3T3 cells) stimulated with the mutated FGF1, methylthiazoletetrazolium (MTT) assay (for example by stimulating serum-starved cells with mutated FGF1 for 24 hr then measuring viable cells), cell number quantification or BrdU incorporation. In some examples, the assay provided by Fu et al., *World J. Gastroenterol.* 10:3590-6, 2004; Klingenberg et al., *J. Biol. Chem.* 274:18081-6, 1999; Shen et al., *Protein Expr Purif* 81:119-25, 2011, or Zou et al., *Chin. Med. J.* 121:424-429, 2008 is used to measure mitogenic activity.

Mutations that reduce the heparan binding affinity (such as a reduction of at least 10%, at least 20%, at least 50%, or at least 75%, e.g., as compared to a native FGF1 protein without the mutation), can also be used to reduce mitogenic activity, for example by substituting heparan binding residues from a paracrine FGFs into a mutant FGF1.

In some examples, an FGF1 mutant includes mutations to the FGF1 nuclear export sequence, for example to decrease the amount of FGF1 in the nucleus and reduce its mitogenicity as measured by thymidine incorporation assays in cultured cells (e.g., see Nilsen et al., *J. Biol. Chem.* 282(36): 26245-56, 2007). Mutations to the nuclear export sequence decrease FGF1-induced proliferation (e.g., see Nilsen et al., *J. Biol. Chem.* 282(36):26245-56, 2007). Methods of measuring FGF1 degradation are known in the art, such as measuring [$^{35}$S] methionine-labeled FGF1 or immunoblotting for steady-state levels of FGF1 in the presence or absence of proteasome inhibitors. In one example, the assay provided by Nilsen et al., *J. Biol. Chem.* 282(36):26245-56, 2007 or Zakrzewska et al., *J. Biol. Chem.* 284:25388-403, 2009 is used to measure FGF1 degradation.

Peptide Modifications

A mutant FGF1 protein (e.g., SEQ ID NO: 10, 11, 12, or 13) can be modified, e.g., to improve stability or its pharmacological profile. Exemplary chemical modifications include, e.g., adding chemical moieties, creating new bonds, and removing chemical moieties. Modifications at amino acid side groups include acylation of lysine ε-amino groups, N-alkylation of arginine, histidine, or lysine, alkylation of glutamic or aspartic carboxylic acid groups, and deamidation of glutamine or asparagine. Modifications of the terminal amino group include the des-amino, N-lower alkyl, N-di-lower alkyl, and N-acyl modifications. Modifications of the terminal carboxyl group include the amide, lower alkyl amide, dialkyl amide, and lower alkyl ester modifications.

In some embodiments, the mutant FGF1 protein (e.g., any of SEQ ID NOS: 10-13) is linked (e.g., attached to) a heparin molecule.

In some examples, the mutant FGF1 protein (e.g., any of SEQ ID NOS: 10-13) is modified to include water soluble polymers, such as polyethylene glycol (PEG), PEG derivatives, polyalkylene glycol (PAG), polysialyic acid, or hydroxyethyl starch).

In some examples, the mutant FGF1 protein is PEGylated at one or more positions, such as at N95 of any of SEQ ID NOS: 10-13 (for example see methods of Niu et al., *J. Chromatog.* 1327:66-72, 2014).

In some examples, the mutant FGF1 protein (e.g., any of SEQ ID NOS: 10-13) includes an immunoglobin Fc domain (for example see Czajkowsky et al., *EMBO Mol. Med.* 4:1015-28, 2012, herein incorporated by reference). The conserved Fc fragment of an antibody can be incorporated either N-terminal or C-terminal of the protein, and can enhance stability of the protein and therefore serum half-life. The Fc domain can also be used as a means to purify the proteins on Protein A or Protein G sepharose beads.

Variant Sequences

Proteins that vary in sequence from the disclosed mutant FGF1 proteins (e.g., SEQ ID NO: 10, 11, 12, or 13) are provided herein. Such variants can contain one or more mutations, such as a single insertion, a single deletion, a single substitution. In one example, such variant peptides are produced by manipulating the nucleotide sequence encoding a peptide using standard procedures such as site-directed mutagenesis or PCR. Such variants can also be chemically synthesized. In some examples, a mutant FGF1 protein includes 1-50 insertions, 1-50 deletions, 1-50 substitutions, and/or any combination thereof (e.g., single substitution together with 1-49 deletions) as compared to a native FGF1 protein. In some examples, the disclosure provides a variant of any disclosed mutant FGF1 protein having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 04, 41, 42, 43, 44, 4, 5, 46, 47, 48, 49 or 50 additional amino acid changes. In some examples, any mutant FGF1 protein provided in SEQ ID NO: 10, 11, 12, or 13 further includes 1-8 amino acid insertions, 1-50 amino acid deletions, 1-50 amino acid substitutions, and/or any combination thereof (e.g., 1-15, 1-4, or 1-5 amino acid deletions together with 1-10, 1-5 or 1-7 amino acid substitutions). In some examples, the disclosure provides a variant of SEQ ID NO: 10, 11, 12, or 13, having 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 04, 41, 42, 43, 44, 4, 5, 46, 47, 48, 49 or 50 amino acid changes, such as amino acid substitutions and/or deletions.

One type of modification or mutation that can be made is the substitution of amino acids for amino acid residues having a similar biochemical property, that is, a conservative substitution (such as 1-4, 1-8, 1-10, 1-20, 5-50, 10-25, or 5-10 conservative substitutions). Typically, conservative substitutions have little to no impact on the activity of a resulting peptide. For example, a conservative substitution is an amino acid substitution in SEQ ID NO: 10, 11, 12, or 13, which does not substantially affect the ability of the peptide to decrease blood glucose in a mammal. An alanine scan can be used to identify which amino acid residues in a mutant FGF1 protein (such as SEQ ID NO: 10, 11, 12, or 13) can tolerate an amino acid substitution. In one example, the blood glucose lowering activity of SEQ ID NO: 10, 11, 12, or 13 is not altered by more than 25%, for example not more than 20%, for example not more than 10%, when an alanine, or other conservative amino acid, is substituted for 1-4, 1-8, 1-10, 1-20, 5-50, 10-25, or 5-10 native amino acids. Examples of amino acids which may be substituted for an original amino acid in a protein and which are regarded as conservative substitutions include: Ser for Ala; Lys, Gln, or Asn for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

More substantial changes can be made by using substitutions that are less conservative, e.g., selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine. The effects of these amino acid substitutions (or other deletions and/or additions) can be assessed by analyzing the function of the variant protein, such as SEQ ID NO: 10, 11, 12, or 13, by analyzing the ability of the variant protein to decrease blood glucose in a mammal.

Generation of Proteins

Isolation and purification of recombinantly expressed mutated FGF1 proteins can be carried out by conventional means, such as preparative chromatography and immunological separations. Once expressed, mutated FGF1 proteins can be purified according to standard procedures, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes.

In addition to recombinant methods, mutated FGF1 proteins disclosed herein can also be constructed in whole or in part using standard peptide synthesis. In one example, mutated FGF1 proteins are synthesized by condensation of the amino and carboxyl termini of shorter fragments. Methods of forming peptide bonds by activation of a carboxyl terminal end (such as by the use of the coupling reagent N, N'-dicylohexylcarbodiimide) are known.

Nucleic Acid Molecules and Vectors

Nucleic acid molecules encoding a mutated FGF1 protein are encompassed by this disclosure. Based on the genetic code, nucleic acid sequences coding for any mutated FGF1 protein, can be routinely generated. In some examples, such a sequence is optimized for expression in a host cell, such as a host cell used to express the mutant FGF1 protein.

A nucleic acid sequence that codes for a mutant FGF1 protein having at least 60%, at least 70%, at least 75%, at least 80%, at least 90%, at least 92%, at least 95%, at least 96%, at least 97%, at least 98%, at least 99%, or 100% sequence identity to SEQ ID NO: 10, 11, 12, or 13, can readily be produced using the amino acid sequences provided herein, and the genetic code. In addition, a variety of clones containing functionally equivalent nucleic acids, such as nucleic acids which differ in sequence but which encode the same mutant FGF1 protein sequence, can be generated.

Nucleic acid molecules include DNA, cDNA, and RNA sequences which encode a mutated FGF1 peptide. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, Biochemistry, 3$^{rd}$ Edition, W. H. 5 Freeman and Co., NY).

Codon preferences and codon usage tables for a particular species can be used to engineer isolated nucleic acid molecules encoding a mutated FGF1 protein (such as one encoding a protein generated using the mutations shown in Table 1, the sequences in SEQ ID NO: 10, 11, 12, or 13, or those encoding a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) that take advantage of the codon usage preferences of that particular species. For example, the proteins disclosed herein can be designed to have codons that are preferentially used by a particular organism of interest.

A nucleic acid encoding the desired protein can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). A variety of cloning and in vitro amplification methodologies can be used. In addition, nucleic acids encoding sequences encoding a desired protein can be prepared by cloning techniques. Examples of appropriate cloning and sequencing techniques, and instructions sufficient to direct persons of skill through cloning are found in Sambrook et al. (ed.), Molecular Cloning: A Laboratory Manual 2nd ed., vol. 1-3, Cold Spring Harbor Laboratory Press, Cold Spring, Harbor, N.Y., 1989, and Ausubel et al., (1987) in "Current Protocols in Molecular Biology," John Wiley and Sons, New York, N.Y.

Nucleic acid sequences encoding a desired protein can be prepared by any suitable method including, for example, cloning of appropriate sequences or by direct chemical synthesis by methods such as the phosphodiester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

In one example, a mutant FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) is prepared by inserting the cDNA which encodes the protein into a vector. The insertion can be made so that the desired protein is read in frame and produced.

The mutated FGF1 nucleic acid coding sequence (such as a sequence encoding SEQ ID NO: 10, 11, 12, or 13, or those encoding a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect, plant, and mammalian organisms. Methods of expressing DNA sequences having eukaryotic or viral sequences in prokaryotes can be used. Biologically functional viral and plasmid DNA vectors capable of expression and replication in a host can be used. The vector can encode a selectable marker, such as a thymidine kinase gene.

Nucleic acid sequences encoding a mutated FGF1 protein (such as encoding SEQ ID NO: 10, 11, 12, or 13, or those encoding a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) can be operatively linked to expression control sequences. An expression control sequence operatively linked to a desired protein coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a mutated FGF1 protein-encoding gene, splicing signal for introns, maintenance of the correct reading frame of that gene to permit proper translation of mRNA, and stop codons.

In one embodiment, vectors are used for expression in yeast such as *S. cerevisiae, P. pastoris*, or *Kluyveromyces*

*lactis*. Several promoters can be used in yeast expression systems such as the constitutive promoters plasma membrane H$^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* can be used, such as pKLAC1. Thus, in one example, after amplification in bacteria, plasmids can be introduced into the corresponding yeast auxotrophs by methods similar to bacterial transformation. The nucleic acid molecules encoding a mutated FGF1 protein (such as a sequence encoding SEQ ID NO: 10, 11, 12, or 13, or those encoding a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) can also be designed to express in insect cells.

A mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast cell lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared that encode a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) Exemplary viral vectors include polyoma, SV40, adenovirus, vaccinia virus, adeno-associated virus, herpes viruses including HSV and EBV, Sindbis viruses, alphaviruses and retroviruses of avian, murine, and human origin. Baculovirus (Autographa californica multinuclear polyhedrosis virus; AcMNPV) vectors can be used. Other suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors, and poliovirus vectors. Specific exemplary vectors are poxvirus vectors such as vaccinia virus, fowlpox virus and a highly attenuated vaccinia virus (MVA), adenovirus, baculovirus, and the like. Pox viruses of use include orthopox, suipox, avipox, and capripox virus. Orthopox include vaccinia, ectromelia, and raccoon pox. One example of an orthopox of use is vaccinia. Avipox includes fowlpox, canary pox, and pigeon pox. Capripox include goatpox and sheeppox. In one example, the suipox is swinepox. Other viral vectors that can be used include other DNA viruses such as herpes virus and adenoviruses, and RNA viruses such as retroviruses and polio.

Viral vectors that encode a mutated FGF1 protein (such as SEQ ID NO: 10, 11, 12, or 13, or encode a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) can include at least one expression control element operationally linked to the nucleic acid sequence encoding the protein. The expression control elements are inserted in the vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the protein in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Recombinant DNA viruses containing a heterologous DNA sequence encoding a mutated FGF1 protein (such as SEQ ID NO: 10, 11, 12, or 13, or those encoding a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) can be prepared. Such techniques involve, for example, homologous recombination between the viral DNA sequences flanking the DNA sequence in a donor plasmid and homologous sequences present in the parental virus. The vector can be constructed, such as by using a unique restriction endonuclease site that is naturally present or artificially inserted in the parental viral vector to insert the heterologous DNA.

When the host is a eukaryote, such methods of transfection of DNA as calcium phosphate coprecipitation, conventional mechanical procedures such as microinjection, electroporation, insertion of a plasmid encased in liposomes, or virus vectors can be used. Eukaryotic cells can also be co-transformed with polynucleotide sequences encoding a mutated FGF1 protein (such as SEQ ID NO: 10, 11, 12, or 13, or those encoding a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). An expression system, such as plasmids and vectors, can be used to produce proteins in cells, including eukaryotic cells, such as the COS, CHO, HeLa and myeloma cell lines.

Recombinant Cells

A nucleic acid molecule encoding a mutated FGF1 protein disclosed herein can be used to transform cells and make transformed cells. Thus, cells expressing a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), are disclosed. Cells expressing a mutated FGF1 protein disclosed herein can be eukaryotic or prokaryotic. Examples of such cells include, but are not limited to bacteria, archea, plant, fungal, yeast, insect, and mammalian cells, such as *Lactobacillus, Lactococcus, Bacillus* (such as *B. subtilis*), *Escherichia* (such as *E. coli*), *Clostridium, Saccharomyces* or *Pichia* (such as *S. cerevisiae* or *P. pastoris*), *Kluyveromyces lactis, Salmonella typhimurium*, SF9 cells, C129 cells, 293 cells, *Neurospora*, and immortalized mammalian myeloid and lymphoid cell lines.

Cells expressing a mutated FGF1 protein are transformed or recombinant cells. Such cells can include at least one exogenous nucleic acid molecule that encodes a mutated FGF1 protein, for example SEQ ID NO: 10, 11, 12, or 13, or those encoding a protein having at least 80%, at least 85%, at least 90%, at least 92%, at least 95%, at least 96%, at least 97%, at least 98%, at least 99%, or 100% sequence identity to SEQ ID NO: 10, 11, 12, or 13. It is understood that all progeny may not be identical to the parental cell since there may be mutations that occur during replication. Methods of stable transfer, meaning that the foreign DNA is continuously maintained in the host cell, can be used.

Transformation of a host cell with recombinant DNA may be carried out by conventional techniques. Where the host is prokaryotic, such as *E. coli*, competent cells which are capable of DNA uptake can be prepared from cells harvested after exponential growth phase and subsequently treated by the $CaCl_2$ method. Alternatively, $MgCl_2$ or RbCl can be used. Transformation can also be performed after forming a protoplast of the host cell if desired, or by electroporation. Techniques for the propagation of mammalian cells in culture can be used (see, Jakoby and Pastan (eds.), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. Techniques for the transformation of yeast cells, such as polyethylene glycol transformation, protoplast transformation, and gene guns, can be used.

Pharmaceutical Compositions

Pharmaceutical compositions that include a mutated FGF1 protein (such as SEQ ID NO: 10, 11, 12, or 13, or a protein having at least at least 80%, at least 85%, 90%, at least 92%, at least 95%, at least 96%, at least 97%, at least 98%, at least 99%, or 100% sequence identity to SEQ ID NO: 10, 11, 12, or 13), or a nucleic acid encoding such as protein, can be formulated with an appropriate pharmaceutically acceptable carrier, depending upon the particular mode of administration chosen.

In some embodiments, the pharmaceutical composition consists essentially of at least one mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) (or a nucleic acid encoding such a protein), or combinations thereof, and a pharmaceutically acceptable carrier. In these embodiments, additional therapeutically effective agents are not included in the compositions.

In one embodiment, the pharmaceutical composition includes at least one mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) (or a nucleic acid encoding such a protein), or combinations thereof, and a pharmaceutically acceptable carrier. Additional therapeutic agents, such as agents for the treatment of diabetes, can be included. Thus, the pharmaceutical compositions can include a therapeutically effective amount of another agent. Examples of such agents include, without limitation, anti-apoptotic substances such as the Nemo-Binding Domain and compounds that induce proliferation such as cyclin dependent kinase (CDK)-6, CDK-4 and cyclin D1. Other active agents can be utilized, such as antidiabetic agents for example, insulin, metformin, sulphonylureas (e.g., glibenclamide, tolbutamide, glimepiride), nateglinide, repaglinide, thiazolidinediones (e.g., rosiglitazone, pioglitazone), peroxisome proliferator-activated receptor (PPAR)-gamma-agonists (such as C1262570, aleglitazar, farglitazar, muraglitazar, tesaglitazar, and TZD) and PPAR-γ antagonists, PPAR-gamma/alpha modulators (such as KRP 297), alpha-glucosidase inhibitors (e.g., acarbose, voglibose), dipeptidyl peptidase (DPP)-IV inhibitors (such as LAF237, MK-431), alpha2-antagonists, agents for lowering blood sugar, cholesterol-absorption inhibitors, 3-hydroxy-3-methylglutaryl-coenzyme A (HMGCoA) reductase inhibitors (such as a statin), insulin and insulin analogues, GLP-1 and GLP-1 analogues (e.g. exendin-4) or amylin. Additional examples include immunomodulatory factors such as anti-CD3 mAb, growth factors such as HGF, VEGF, PDGF, lactogens, and PTHrP. In some examples, the pharmaceutical compositions containing a mutated FGF1 protein can further include a therapeutically effective amount of other FGFs, such as FGF21, FGF19, or both, heparin, or combinations thereof.

The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). For instance, parenteral formulations usually include injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

In some embodiments, a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) is included in a controlled release formulation, for example, a microencapsulated formulation. Various types of biodegradable and biocompatible polymers, methods can be used, and methods of encapsulating a variety of synthetic compounds, proteins and nucleic acids, have been described (see, for example, U.S. Patent Publication Nos. 2007/0148074; 2007/0092575; and 2006/0246139; U.S. Pat. Nos. 4,522,811; 5,753,234; and 7,081,489; PCT Publication No. WO/2006/052285; Benita, *Microencapsulation: Methods and Industrial Applications*, $2^{nd}$ ed., CRC Press, 2006).

In other embodiments, a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) is included in a nanodispersion system. Exemplary nanodispersion systems and methods for producing such nanodispersions are provided in e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid (PLGA), poly (ethylene glycol). Exemplary low molecular weight surfactants include sodium dodecyl sulfate, hexadecyl pyridinium chloride, polysorbates, sorbitans, poly(oxyethylene) alkyl ethers, poly(oxyethylene) alkyl esters, and combinations thereof. In one example, the nanodispersion system includes PVP and ODP or a variant thereof (such as 80/20 w/w). In some examples, the nanodispersion is prepared using the solvent evaporation method, see for example, Kanaze et al., *Drug Dev. Indus. Pharm.* 36:292-301, 2010; Kanaze et al., *J. Appl. Polymer Sci.* 102:460-471, 2006.

With regard to the administration of nucleic acids, one approach to administration of nucleic acids is direct treatment with plasmid DNA, such as with a mammalian expression plasmid. As described above, the nucleotide sequence encoding a mutated FGF1 protein (such as encoding SEQ ID NO: 10, 11, 12, or 13, or encoding a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), can be placed under the control of a promoter to increase expression of the protein.

Many types of release delivery systems can be used. Examples include polymer based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or polynucleotide encoding such a protein, is contained in a form within a matrix such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Use of a long-term sustained release implant can be suitable for treatment of chronic conditions, such as diabetes. Long-term release, as used herein, means that the implant is constructed and arranged to deliver therapeutic levels of the active ingredient for at least 30 days, such as 60 days. Long-term sustained release implants include the release systems described above. These systems have been described for use with nucleic acids (see U.S. Pat. No. 6,218,371). For use in vivo, nucleic acids and peptides are preferably relatively resistant to degradation (such as via endo- and exo-nucleases). Thus, modifications of the disclosed mutated FGF1 proteins, such as the inclusion of a C-terminal amide, can be used.

The dosage form of the pharmaceutical composition can be determined by the mode of administration chosen. For instance, in addition to injectable fluids, topical, inhalation, oral, and suppository formulations can be employed. Topical preparations can include eye drops, ointments, sprays, patches, and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, cellulose, starch, or magnesium stearate.

The pharmaceutical compositions that include a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), can be formulated in unit dosage form, suitable for individual administration of precise dosages.

In one non-limiting example, a unit dosage contains from about 1 mg to about 1 g of a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), such as about 10 mg to about 100 mg, about 50 mg to about 500 mg, about 100 mg to about 900 mg, about 250 mg to about 750 mg, or about 400 mg to about 600 mg. In other examples, a therapeutically effective amount of a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) is about 0.01 mg/kg to about 50 mg/kg, for example, about 0.5 mg/kg to about 25 mg/kg, about 0.5 mg/kg to about 1 mg/kg, about 0.5 mg/kg to about 5 mg/kg, about 0.05 mg/kg to about 0.1 mg/kg, about 0.01 mg/kg to about 0.1 mg/kg, or about 1 mg/kg to about 10 mg/kg. In other examples, a therapeutically effective amount of a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) is about 0.1 mg/kg to about 1 mg/kg, for example about 0.5 mg/kg, about 0.63 mg/kg, or about 1 mg/kg. In a particular example, a therapeutically effective amount of a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) includes about 0.01 mg/kg to about 0.5 mg/kg, such as about 0.1 mg/kg, or about 0.5 mg/kg.

Methods of Treatment

The disclosed mutated FGF1 proteins (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or nucleic acids encoding such proteins, can be administered to a subject, for example to treat a metabolic disease, for example by reducing fed and fasting blood glucose, improving insulin sensitivity and glucose tolerance, reducing systemic chronic inflammation, ameliorating hepatic steatosis in a mammal, or combinations thereof.

The compositions of this disclosure that include a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or nucleic acids encoding these proteins, can be administered to humans or other animals by any means, including orally, intravenously, intramuscularly, intraperitoneally, intranasally, intradermally, intrathecally, subcutaneously, via inhalation or via suppository. In one non-limiting example, the composition is administered via injection. In some examples, site-specific administration of the composition can be used, for example by administering a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or a nucleic acid encoding such a protein, to adipose tissue (for example by using a pump, or by implantation of a slow release form at the adipose depot). The particular mode of administration and the dosage regimen will be selected by the attending clinician, taking into account the particulars of the case (e.g. the subject, the disease, the disease state involved, the particular treatment, and whether the treatment is prophylactic). Treatment can involve daily or multi-daily or less than daily (such as weekly, every other week, monthly, every 7 days, every 10 days, every 14 days, every 21 days, every 30 days, every 40 days, every 60 days, etc.) doses of the mutant FGF1 over a period of a few days, few weeks, to months, or even years. For example, a therapeutically effective amount of a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13) can be administered in a single dose, once daily, twice daily, three times daily, four times daily, six times daily, weekly, every other week, every three weeks, every month, every other month, or in several doses, for example daily, or during a course of treatment. In a particular non-limiting example, treatment involves once daily dose, twice daily dose, once weekly dose, every other week dose, or monthly dose.

The amount of a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), administered can be dependent on the subject being treated, the severity of the affliction, and the manner of administration, and can be left to the judgment of the prescribing clinician. The formulation to be administered contains a quantity of the mutated FGF1 protein in amounts effective to achieve the desired effect in the subject being treated. A therapeutically effective amount of a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), can be the amount of the protein (or a nucleic acid encoding these proteins) that is necessary to treat diabetes or reduce blood glucose levels (for example a reduction of at least 5%, at least 10% or at least 20%, for example relative to no administration of the mutant FGF1).

When a viral vector is utilized for administration of a nucleic acid encoding a mutated FGF1 protein (such as SEQ ID NO: 10, 11, 12, or 13, or those encoding a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), the recipient can receive a dosage of each recombinant virus in the composition in the range of from about $10^5$ to about $10^{10}$ plaque forming units/mg mammal, although a lower or higher dose can be administered. Examples of methods for administering the composition into mammals include, but are not limited to, exposure of cells to the recombinant virus ex vivo, or injection of the composition into the affected tissue or intravenous, subcutaneous, intradermal, or intramuscular administration of the virus. Alternatively the recombinant viral vector or combination of recombinant viral vectors may be administered locally by direct injection into the pancreas in a pharmaceutically acceptable carrier.

Generally, the quantity of recombinant viral vector, carrying the nucleic acid sequence of the mutated FGF1 protein to be administered (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), is based on the titer of virus particles. An exemplary range to be administered is $10^5$ to $10^{10}$ virus particles per mammal, such as a human.

In some examples, a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or a nucleic acid encoding the mutated FGF1 protein, is administered in combination (such as sequentially or simultaneously or contemporaneously) with one or more other agents, such as those useful in the treatment of diabetes or insulin resistance (e.g., insulin).

Anti-diabetic agents are generally categorized into six classes: biguanides (e.g., metformin); thiazolidinediones (including rosiglitazone (Avandia®), pioglitazone (Actos®), rivoglitazone, and troglitazone); sulfonylureas; inhibitors of carbohydrate absorption; fatty acid oxidase inhibitors and anti-lipolytic drugs; and weight-loss agents. Any of these agents can also be used in the methods disclosed herein. The anti-diabetic agents include those agents disclosed in *Diabetes Care,* 22(4):623-634. One class of anti-diabetic agents of use is the sulfonylureas, which are believed to increase secretion of insulin, decrease hepatic glucogenesis, and increase insulin receptor sensitivity. Another class of anti-diabetic agents is the biguanide antihyperglycemics, which decrease hepatic glucose production and intestinal absorption, and increase peripheral glucose uptake and utilization, without inducing hyperinsulinemia.

In some examples, a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), can be administered in combination with effective doses of anti-diabetic agents (such as biguanides, thiazolidinediones, or incretins) and/or lipid lowering compounds (such as statins or fibrates). The terms "administration in combination," "co-administration," or the like, refer to both concurrent (e.g., contemporaneous) and sequential administration of the active agents. Administration of a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or a nucleic acid encoding such a protein, may also be in combination with lifestyle modifications, such as increased physical activity, low fat diet, low sugar diet, and smoking cessation.

Additional agents that can be used in combination with the disclosed mutated FGF1 proteins include, without limitation, anti-apoptotic substances such as the Nemo-Binding Domain. Other active agents can be utilized, such as antidiabetic agents for example, insulin, metformin, sulphonylureas (e.g., glibenclamide, tolbutamide, glimepiride), nateglinide, repaglinide, thiazolidinediones (e.g., rosiglitazone, pioglitazone), peroxisome proliferator-activated receptor (PPAR)-gamma-agonists (such as C1262570) and antagonists, PPAR-gamma/alpha modulators (such as KRP 297), alpha-glucosidase inhibitors (e.g., acarbose, voglibose), Dipeptidyl peptidase (DPP)-IV inhibitors (such as LAF237, MK-431), alpha2-antagonists, agents for lowering blood sugar, cholesterol-absorption inhibitors, 3-hydroxy-3-methylglutaryl-coenzyme A (HMGCoA) reductase inhibitors (such as a statin), insulin and insulin analogues, GLP-1 and GLP-1 analogues (e.g., exendin-4) or amylin. In some embodiments the agent is an immunomodulatory factor such as anti-CD3 mAb, growth factors such as HGF, vascular endothelial growth factor (VEGF), platelet derived growth factor (PDGF), lactogens, or parathyroid hormone related protein (PTHrP). In one example, the mutated FGF1 protein is administered in combination with a therapeutically effective amount of another FGF, such as FGF21, FGF19, or both, heparin, or combinations thereof. In one example, a mutated FGF1 provided herein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13, or a nucleic acid encoding the protein) is administered in combination with a therapeutically effective amount of another mutant FGF, such as one provided in any of U.S. Pat. Nos. 8,906,854; 8,999,929; 9,925,241, and 9,925,243; US Patent Application Publication No. US-2016-0237133-A1; US-2017-0355739-A1; US-2018-0057554-A1; US-2018-0228869-A1; US 2018-0050087 A1; and US-2019-0151416-A1, and PCT Publication WO 2018/112200.

In some embodiments, methods are provided for treating diabetes or pre-diabetes in a subject by administering a therapeutically effective amount of a composition including a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or a nucleic acid encoding the protein, to the subject. The subject can have diabetes type I or diabetes type II. The subject can be any mammalian subject, including human subjects and veterinary subjects such as cats and dogs. The subject can be a child or an adult. The subject can also be administered insulin. The method can include measuring blood glucose levels.

In some examples, the method includes selecting a subject with diabetes, such as type I or type II diabetes, or a subject at risk for diabetes, such as a subject with pre-diabetes. These subjects can be selected for treatment with the disclosed mutated FGF1 proteins (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or nucleic acid molecules encoding such.

In some examples, a subject with diabetes may be clinically diagnosed by a fasting plasma glucose (FPG) concentration of greater than or equal to 7.0 millimole per liter (mmol/L) (126 milligram per deciliter (mg/dL)), or a plasma glucose concentration of greater than or equal to 11.1 mmol/L (200 mg/dL) at about two hours after an oral glucose tolerance test (OGTT) with a 75 gram (g) load, or in a patient with classic symptoms of hyperglycemia or hyperglycemic crisis, a random plasma glucose concentration of greater than or equal to 11.1 mmol/L (200 mg/dL), or HbA1c levels of greater than or equal to 6.5%. In other examples, a subject with pre-diabetes may be diagnosed by impaired glucose tolerance (IGT). An OGTT two-hour plasma glucose of greater than or equal to 140 mg/dL and less than 200 mg/dL (7.8-11.0 mM), or a fasting plasma glucose (FPG) concentration of greater than or equal to 100 mg/dL and less than 125 mg/dL (5.6-6.9 mmol/L), or HbA1c levels of greater than or equal to 5.7% and less than 6.4% (5.7-6.4%) is considered to be IGT, and indicates that a subject has pre-diabetes. Additional information can be found in *Standards of Medical Care in Diabetes*-2010 (American Diabetes Association, *Diabetes Care* 33:S11-61, 2010).

In some examples, the subject treated with the disclosed compositions and methods has HbA1C of greater than 6.5% or greater than 7%.

In some examples, treating diabetes includes one or more of increasing glucose tolerance (such as an increase of at least 5%, at least 10%, at least 20%, or at least 50%, for example relative to no administration of the mutant FGF1), decreasing insulin resistance (for example, decreasing plasma glucose levels, decreasing plasma insulin levels, or a combination thereof, such as decreases of at least 5%, at least 10%, at least 20%, or at least 50%, for example relative to no administration of the mutant FGF1), decreasing serum triglycerides (such as a decrease of at least 10%, at least 20%, or at least 50%, for example relative to no administration of the mutant FGF1), decreasing free fatty acid levels (such as a decrease of at least 5%, at least 10%, at least 20%, or at least 50%, for example relative to no administration of the mutant FGF1), and decreasing HbA1c levels in the subject (such as a decrease of at least 0.5%, at least 1%, at least 1.5%, at least 2%, or at least 5% for example relative to no administration of the mutant FGF1). In some embodiments, the disclosed methods include measuring glucose tolerance, insulin resistance, plasma glucose levels, plasma insulin levels, serum triglycerides, free fatty acids, and/or HbA1c levels in a subject.

In some examples, administration of a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or nucleic acid molecule encoding such, treats a metabolic disease, such as diabetes (such as type II diabetes) or pre-diabetes, by decreasing of HbA1C, such as a reduction of at least 0.5%, at least 1%, or at least 1.5%, such as a decrease of 0.5% to 0.8%, 0.5% to 1%, 1 to 1.5% or 0.5% to 2%. In some examples the target for HbA1C is less than about 6.5%, such as about 4-6%, 4-6.4%, or 4-6.2%. In some examples, such target levels are achieved within about 26 weeks, within about 40 weeks, or within about 52 weeks. Methods of measuring HbA1C are routine, and the disclosure is not limited to particular methods. Exemplary methods include HPLC, immunoassays, and boronate affinity chromatography.

In some examples, administration of a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or nucleic acid molecule encoding such, treats diabetes or pre-diabetes by increasing glucose tolerance, for example, by decreasing blood glucose levels (such as two-hour plasma glucose in an OGTT or FPG) in a subject. In some examples, the method includes decreasing blood glucose by at least 5% (such as at least 10%, at least 15%, at least 20%, at least 25%, at least 30%, at least 35%, or more) as compared with a control (such as no administration of any of insulin, a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or a nucleic acid molecule encoding such). In particular examples, a decrease in blood glucose level is determined relative to the starting blood glucose level of the subject (for example, prior to treatment with a mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or nucleic acid molecule encoding such). In other examples, decreasing blood glucose levels of a subject includes reduction of blood glucose from a starting point (for example greater than about 126 mg/dL FPG or greater than about 200 mg/dL OGTT two-hour plasma glucose) to a target level (for example, FPG of less than 126 mg/dL or OGTT two-hour plasma glucose of less than 200 mg/dL). In some examples, a target FPG may be less than 100 mg/dL. In other examples, a target OGTT two-hour plasma glucose may be less than 140 mg/dL. Methods to measure blood glucose levels in a subject (for example, in a blood sample from a subject) are routine.

In other embodiments, the disclosed methods include comparing one or more indicators of diabetes (such as glucose tolerance, triglyceride levels, free fatty acid levels, or HbA1c levels) to a control (such as no administration of any of insulin, any mutated FGF1 protein (such as SEQ ID NO: 10, 11, 12, or 13, or a protein having at least 80%, at least 85%, at least 90%, at least 92%, at least 95%, at least 96%, at least 97%, at least 98%, at least 99%, or 100% sequence identity to SEQ ID NO: 10, 11, 12, or 13), or a nucleic acid molecule encoding such), wherein an increase or decrease in the particular indicator relative to the control (as discussed above) indicates effective treatment of diabetes. The control can be any suitable control against which to compare the indicator of diabetes in a subject. In some embodiments, the control is a sample obtained from a healthy subject (such as a subject without diabetes). In some embodiments, the control is a historical control or standard reference value or range of values (such as a previously tested control sample, such as a group of subjects with diabetes, or group of samples from subjects that do not have diabetes). In further examples, the control is a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval). In other examples, the control is the subject (or group of subjects) treated with placebo compared to the same subject (or group of subjects) treated with the therapeutic compound in a cross-over study. In further examples, the control is the subject (or group of subjects) prior to treatment.

The disclosure is illustrated by the following non-limiting Examples.

Example 1

Preparation of Proteins

Mutated FGF1 proteins can be made using known methods (e.g., see Xia et al., *PLoS One.* 7(11):e48210, 2012). An example is provided below.

Briefly, a nucleic acid sequence encoding an FGF1 native or mutant protein (e.g., any of SEQ ID NOS: 1-13), can be fused downstream of an enterokinase (EK) recognition sequence ($Asp_4Lys$) preceded by a flexible 20 amino acid linker (derived from the S-tag sequence of pBAC-3) and an N-terminal $(His)_6$ tag. The resulting expressed fusion protein utilizes the $(His)_6$ tag for efficient purification and can be subsequently processed by EK digestion to yield the protein.

The protein can be expressed from an *E. coli* host after induction with isopropyl-β-D-thio-galactoside. The expressed protein can be purified utilizing sequential column chromatography on Ni-nitrilotriacetic acid (NTA) affinity resin followed by ToyoPearl HW-40S size exclusion chromatography. The purified protein can be digested with EK to remove the N-terminal $(His)_6$ tag, 20 amino acid linker, and $(Asp_4Lys)$ EK recognition sequence. A subsequent second Ni-NTA chromatographic step can be utilized to remove the released N-terminal protein (along with any uncleaved fusion protein). Final purification can be performed using HiLoad Superdex 75 size exclusion chromatography equilibrated to 50 mM $Na_2PO_4$, 100 mM NaCl, 10 mM $(NH_4)_2SO_4$, 0.1 mM ethylenediaminetetraacetic acid (EDTA), 5 mM L-Methionine, pH at 6.5 ("PBX" buffer); L-Methionine can be included in PBX buffer to limit oxidization of reactive thiols and other potential oxidative degradation.

In some examples, the enterokinase is not used, and instead, a protein (such as one that includes an N-terminal methionine) can be made and purified using heparin affinity chromatography.

For storage and use, the purified protein can be sterile filtered through a 0.22 micron filter, purged with $N_2$, snap frozen in dry ice and stored at −80° C. prior to use. The purity of the resulting protein can be assessed by both Coomassie Brilliant Blue and Silver Stain Plus (BIO-RAD Laboratories, Inc., Hercules Calif.) stained sodium dodecyl sulfate polyacrylamide gel electrophoresis (SDS PAGE). Proteins can be prepared in the absence of heparin. Prior to IV bolus, heparin, or PBS, can be added to the therapeutic protein.

In some examples, an FGF1 protein (e.g., any one of SEQ ID NOS: 1-13), can be expressed in *Escherichia coli* cells and purified from the soluble bacterial cell lysate fraction by heparin affinity, ion exchange, and size exclusion chromatography.

Example 2

FGF1 Mutant Proteins Have Reduced Mitogenic Activity

This example describes a cell proliferation assay for measuring the ability of FGF1 mutant and native proteins provided herein (e.g., any of SEQ ID NOS: 1-13, or variants thereof), to reduce mitogenic activity. Similar methods can be used to test other FGF1 mutant proteins. Other exemplary methods are provided in Scarlett et al., *Nat. Med.* 22:800, 2016.

Low passage NIH-3T3 cells are cultured in 10% FBS DMEM high glucose until 70-80% confluence. On day 1, cells are trypsinized and plated in white wall 96-well plate at 5000 cells/well in 10% FBS DMEM high glucose medium (100 μl per well). 24 hours later, cells are washed in PBS and the medium is replaced with proliferation medium (DMEM high glucose without FBS, 25 μg/ml sodium heparin) and increasing concentrations of human recombinant FGF1 (SEQ ID NO: 5) or FGF1 mutant proteins (SEQ ID NOS: 10-13) (0, 0.00001, 0.0001, 0.001, 0.002, 0.005, 0.01, 0.1, 0.5, 1, 10, 50 ng/ml, final concentrations, 100 μl total final volume). Cells are llowed to proliferate for 24 hours. Cellular proliferation is measured by direct addition of 50 ul of CellTiter Glo reagent into the 100 μl of medium. Luminance is quantified after 10-minute incubation at room temperature. The luminance is plotted against Log 2 transformed concentration and fitted with 3-parameter curve fitting algorithm using Graphpad Prism.

As shown in FIGS. 3A-3D, all four of the mutant FGF1 proteins with selective FGFR1b activity have reduced mitogenicity relative to the native FGF1 protein (SEQ ID NO: 5).

Example 3

FGF1 Mutant Proteins Have Anti-Lipolytic Activity

This example describes a lipolysis assay for measuring the ability of FGF1 mutant and native proteins provided herein (e.g., any of SEQ ID NOS: 1-13, or variants thereof), to reduce lipolytic activity through reducing the expression of the key lipolytic enzyme, hormone sensitive lipase (HSL). Similar methods can be used to test other FGF1 mutant proteins.

3T3-L1 derived adipocytes were cultured in maintenance media (10% FBS in DMEM/F12, 5 μg/ml insulin) with 20 nM dexamethasone to induce insulin resistance. The 3T3-L1 cells in complete nutrition media (10% FBS high glucose DMEM+5 ug/ml insulin) were treated with 20 nM Dex together with human recombinant FGF1 (SEQ ID NO: 5) or FGF1 mutant protein (SEQ ID NOS: 10-13) (100 ng/ml) for 48 hours. Cells were harvested for RNA extraction and QPCR measuring HSL (Lipe) expression normalized to 36b4 (a ribosomal housekeeping gene).

Figure 4:
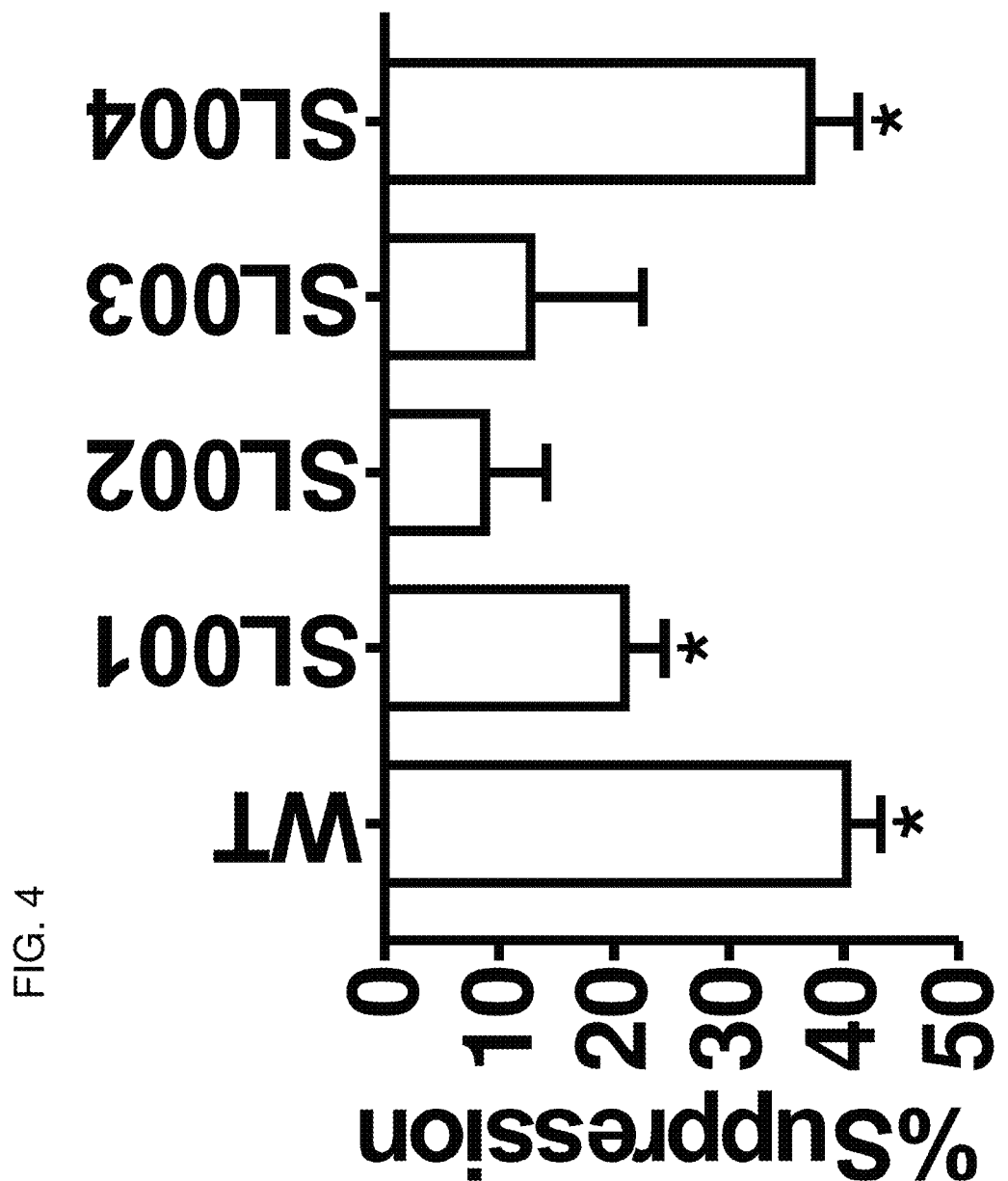
FIG. 4 is a graph showing suppression of HSL (Lipe) expression by mature FGF1 (WT, SEQ ID NO: 5) or FGF1 mutant proteins (SEQ ID NOS: 10-13) in dexamethasone-induced insulin resistant adipocytes. SL001 and SL004 proteins retained the ability to statistically suppress HSL expression (* $p<0.5$).

As shown in FIG. 4, all four of the mutant FGF1 proteins with selective FGFR1b activity suppressed HSL (Lipe expression) compared to vehicle treated cells.

Example 4

Glucose Lowering Ability is Dependent on ATGL Expression

This example describes methods for measuring the ability of FGF1 mutant and native proteins provided herein (e.g., any of SEQ ID NOS: 1-13, or variants thereof), to lower blood glucose in vivo in WT and adipose-specific ATGL KO mice. Similar methods can be used to test other FGF1 mutant proteins.

Mice are housed in a temperature-controlled environment with a 12-hour light/12-hour dark cycle and handled according to institutional guidelines complying with U.S. legislation. To generate adipose-specific Pnpla2 (ATGL) deletion mice, adiponectin-cre (B6;FVB-Tg(Adipoq-cre)1Evdr/J; Stock: 010803) mice were crossed to Pnpla2 flox/flox (B6N.129S-Pnpla2tmlEek/J; Stock: 024278) mice. For diet-induced obesity studies, high fat diet (HFD) (60% fat, F3282; Bio-Serv) was used. The development of diabetes was monitored by daily random fed blood glucose measurement. Mice with moderate T2D (defined by random fed blood glucose ~200 mg/dL) were selected for further study.

Recombinant SL001 protein (SEQ ID NO: 10) or PBS was reconstituted in phosphate buffer saline to a final concentration of 0.2 mg/ml, and injected subcutaneously at 0.5 mg/kg. Blood glucose was monitored at indicated times after injection. Unless otherwise noted, mice were allowed free access to food and water throughout the experiment.

As shown in FIG. 5A, SL001 (SEQ ID NO: 10) lowered blood glucose in wild-type mice with moderate T2D after four hours. However, this ability was lost in adATGL KO mice (FIG. 5B). Thus, the ability of SL001 to lower blood glucose was dependent on expression of ATGL in adipose tissue. The ability of FGF1, including the disclosed FGF1 mutant proteins, to suppress adipose lipolysis is needed for its ability to lower blood glucose. ATGL along with HSL are key enzymes in releasing free fatty acids from adipose triglyceride stores. Knocking out ATGL compromises adipose lipolysis such that the subsequent addition of a mutant FGF1 protein does not further lower lipolysis, and thereby glucose levels. This indicates that the ability of FGF1 and mutants thereof to suppress lipolysis is required for glucose lowering.

Example 5

Glucose Lowering Ability is Independent of adIR Expression

This example describes methods for measuring the ability of FGF1 mutant and native proteins provided herein (e.g., any of SEQ ID NOS: 1-13, or variants thereof), to lower blood glucose in vivo in WT and adipose insulin receptor (adIR) KO mice. Similar methods can be used to test other FGF1 mutant proteins.

Mice were housed in a temperature-controlled environment with a 12 h light/12 h dark cycle and handled according to institutional guidelines complying with U.S. legislation. To generate adipose-specific Insr deletion mice, adiponectin-cre (B6;FVB-Tg(Adipoq-cre)1Evdra; Stock: 010803) mice were crossed to Insr flox/flox (B6.129S4(FVB)-Insr$^{tm1Khn}$/J; Stock: 006955) mice. For diet-induced obesity studies, high fat diet (HFD) (60% fat, F3282; Bio-Serv) was used. The development of diabetes was monitored by daily random fed blood glucose measurement. Mice with moderate T2D (defined by random fed blood glucose ~300 mg/dL) were selected for further study.

Recombinant SL001 protein (SEQ ID NO: 10) or PBS was reconstituted in phosphate buffer saline to a final concentration of 0.2 mg/ml, and injected subcutaneously at 0.5 mg/kg. Blood glucose was monitored at indicated times after injection. Unless otherwise noted, mice were allowed free access to food and water throughout the experiment.

Figure 6:
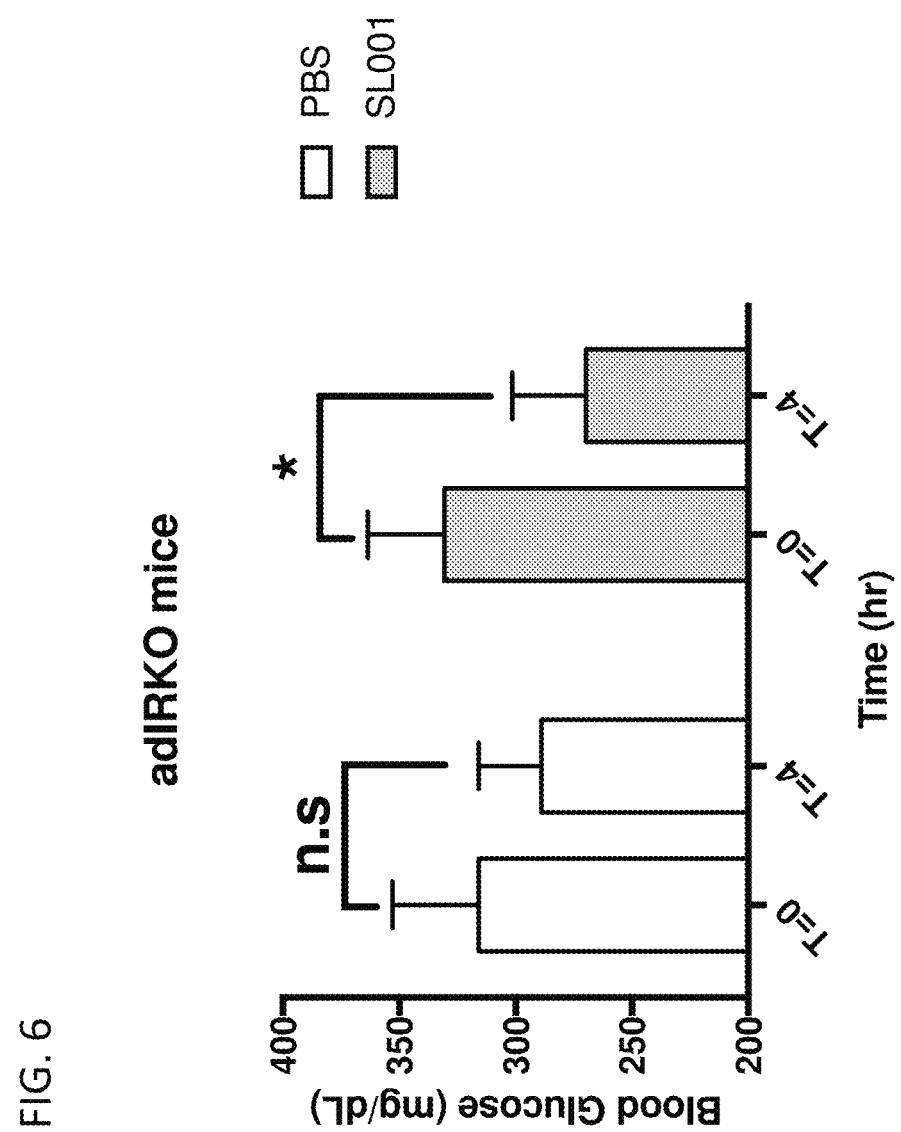
FIG. 6 is a graph showing that the acute glucose lowering ability of SL001 (SEQ ID NO: 10) is independent of adipose insulin receptor (IR) expression (* $p<0.5$).

As shown in FIG. 6 SL001 (SEQ ID NO: 10) retained the ability to lower blood glucose in adipose insulin receptor (adIR) KO mice with moderate T2D after four hours. Insulin is an anti-lipolytic factor. These results indicate FGF1, and the mutant FGF1 proteins provided herein, is also anti-lipolytic factor, as the data demonstrate that the mechanism of glucose lowering by the FGF1 mutant proteins is not via insulin signaling in adipose tissue (is not directly activating the insulin receptor). Instead, FGF1 and the mutant FGF1 proteins provided herein, reduce the expression of lipolytic genes and function transcriptionally, in contrast to insulin which acts post-transcriptionally.

Example 6

Glucose Lowering Ability is Dependent on FGFR1b Expression

This example describes methods for measuring the ability of FGF1 mutant and native proteins provided herein (e.g., any of SEQ ID NOS: 1-13, or variants thereof), to lower blood glucose in vivo in WT and FGFR1b KO mice. Similar methods can be used to test other FGF1 mutant proteins.

Mice are housed in a temperature-controlled environment with a 12-hour light/12-hour dark cycle and handled according to institutional guidelines complying with U.S. legislation. To generate adipose-specific FGFR1b deletion mice, whole body FGFR1b knockout mice (Partanen et al., Genes Dev. 1998 12(15):2332-44) were backcrossed to wildtype mice to generate FGFR1b heterozygous mice, which were subsequently crossed to adipose specific FGFR1 KO mice. For diet-induced obesity studies, high fat diet (HFD) (60% fat, F3282; Bio-Serv) was used. The development of diabetes was monitored by daily random fed blood glucose measurement. Mice with moderate T2D (defined by random fed blood glucose ~300 mg/dL) were selected for further study.

Recombinant SL001 protein (SEQ ID NO: 10) or PBS was reconstituted in phosphate buffer saline to a final concentration of 0.2 mg/ml, and injected subcutaneously at 0.5 mg/kg. Blood glucose was monitored at indicated times after injection. Unless otherwise noted, mice were allowed free access to food and water throughout the experiment.

Figure 7A:
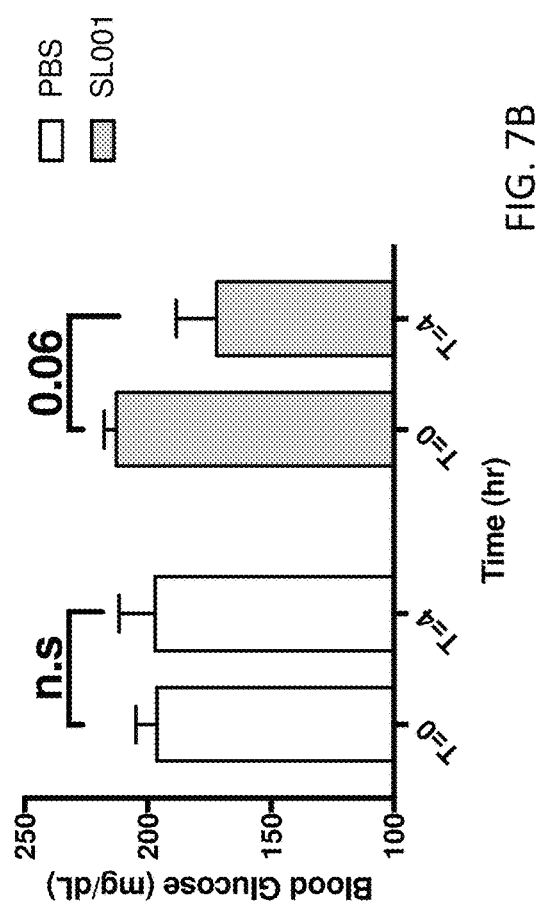
FIGS. 7A-7B are graphs showing that the glucose lowering ability of FGF1 mutant SL001 (SEQ ID NO: 10) is dependent on adipose FGFR1b expression. (A) Blood glucose levels in mice with heterozygous expression of FGFR1b in adipose tissue (adR1bHet) with moderate type 2 diabetes (T2D), before and 4 hours after treatment with PBS or SL001. (B) Blood glucose levels in mice with adipose-specific knockout of FGFR1b (adR1bKO) with T2D, before and 4 hours after treatment with PBS or SL001.
Figure 7B:
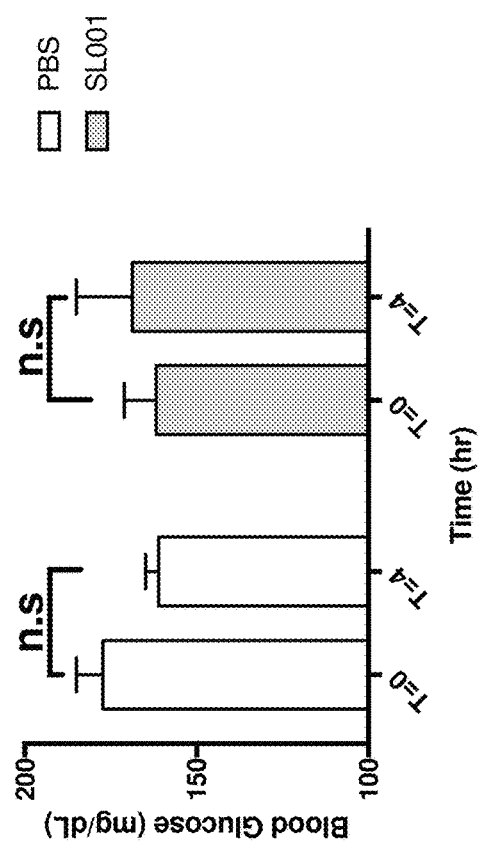

As shown in FIG. 7A, SL001 (SEQ ID NO: 10) was able to lower blood glucose in wild-type mice with moderate T2D after four hours. However, this ability was lost in adipose FGFR1b KO mice (FIG. 7B). Thus, the ability of SL001 to lower blood glucose was dependent on expression of FGFR1b in adipose tissue.

Figure 8A:
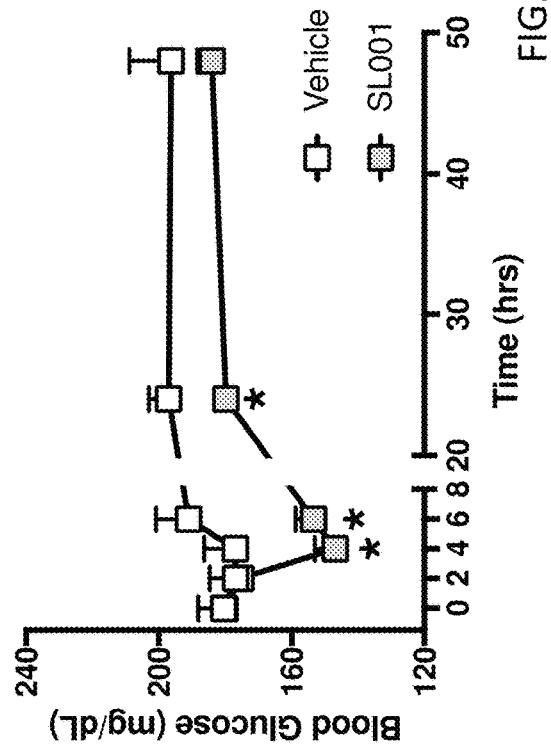
FIGS. 8A-8B are graphs showing that the ability of FGF1 mutant SL001 (SEQ ID NO: 10) to sustain glucose lowering is dependent on adipose FGFR1b expression. (A) Blood glucose levels in mice with heterozygous expression of FGFR1b in adipose tissue (adR1bHet) with moderate type 2 diabetes (T2D), before and up to 50 hours after treatment with PBS or SL001. (B) Blood glucose levels in adipose FGFR1b KO type mice with T2D, before and up to 50 hours after treatment with PBS or SL001 (* $p<0.5$).
Figure 8B:
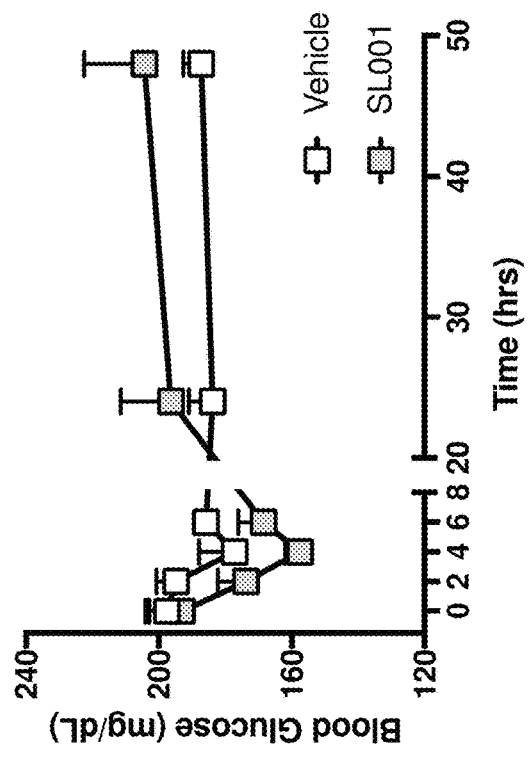

As shown in FIG. 8A, SL001 (SEQ ID NO: 10) was able to sustain blood glucose lowering in wild-type mice with moderate T2D for at least 24 hours. However, this ability was lost in adipose FGFR1b KO mice (FIG. 8B). Thus, the ability of SL001 to sustain blood glucose lowering is dependent on expression of FGFR1b in adipose tissue.

Based on these results, FGF1 mutant proteins, such as SEQ ID NOS: 10-13, can be used to lower blood glucose in vivo for extended periods of time.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A method of reducing blood glucose in a mammal, comprising:
   administering to the mammal a therapeutically effective amount of a mutated mature fibroblast growth factor (FGF) 1 protein comprising at least 95% sequence identity to SEQ ID NO: 10, and retaining the N7H, N18D, D32E, Y64C, F85L, E90G, K101R, and N114S amino acid substitutions, thereby reducing the blood glucose.

2. The method of claim 1, wherein the method reduces fed and fasting blood glucose, improves insulin sensitivity and glucose tolerance, reduces systemic chronic inflammation, ameliorates hepatic steatosis in a mammal, or combinations thereof.

3. The method of claim 1, wherein the therapeutically effective amount of the mutated mature FGF1 protein is at least 0.1 mg/kg.

4. The method of claim 1, wherein the administering is subcutaneous, intraperitoneal, intramuscular, intravenous or intrathecal.

5. The method of claim 1, wherein the mammal is a human, cat or dog.

6. The method of claim 1, wherein the method further comprises administering to the subject a therapeutically effective amount of an additional therapeutic compound.

7. The method of claim 6, wherein the additional therapeutic compound is insulin, an alpha-glucosidase inhibitor, amylin agonist, dipeptidyl-peptidase 4 (DPP-4) inhibitor, meglitinide, sulfonylurea, or a peroxisome proliferator-activated receptor (PPAR)-gamma agonist.

8. The method of claim 7, wherein the PPAR-gamma agonist is a thiazolidinedione (TZD), aleglitazar, farglitazar, muraglitazar, or tesaglitazar.

9. The method of claim 8, wherein the TZD is pioglitazone, rosiglitazone, rivoglitazone, or troglitazone.

10. The method of claim 7, wherein the mutated mature FGF1 protein has decreased mitogenicity compared to a native mature FGF1 protein (SEQ ID NO: 2, 4, 5, 6, 7, 8 or 9); increased blood glucose lowering ability compared to a native mature FGF1 protein (SEQ ID NO: 2, 4, 5, 6, 7, 8 or 9); or both.

11. The method of claim 1, wherein the mutated mature FGF1 protein is 90 to 140 amino acids in length.

12. The method of claim 1, wherein the mutated mature FGF1 protein comprises a deletion of 6, 7, 8, 9, 10, 11, or 12 contiguous N-terminal amino acids from a native FGF1 protein.

13. The method of claim 12, wherein the deleted contiguous N-terminal amino acids are replaced with the amino acid sequence comprising or consisting of MRDSSPL (SEQ ID NO: 14), SYNHLQGDVR (SEQ ID NO: 15), SYNHLQGDVRV (SEQ ID NO: 16), or SYDYMEGGDIRV (SEQ ID NO: 17).

14. The method of claim 1, wherein the mutated mature FGF1 protein further comprises at least one additional amino acid substitution selected from N7H, K10E, L13P, G19R, L44P, S76P, I98T, K113Q, and K118E.

15. The method of claim 1, wherein the mutated mature FGF1 protein comprises at least 96% sequence identity to SEQ ID NO: 10, and retains the N7H, N18D, D32E, Y64C, F85L, E90G, K101R, and N114S amino acid substitutions.

16. The method of claim 1, wherein the mutated mature FGF1 protein comprises at least 97% sequence identity to SEQ ID NO: 10, and retains the N7H, N18D, D32E, Y64C, F85L, E90G, K101R, and N114S amino acid substitutions.

17. The method of claim 1, wherein the mutated mature FGF1 protein comprises at least 98% sequence identity to SEQ ID NO: 10, and retains the N7H, N18D, D32E, Y64C, F85L, E90G, K101R, and N114S amino acid substitutions.

18. The method of claim 1, wherein the mutated mature FGF1 protein comprises at least 99% sequence identity to SEQ ID NO: 10, and retains the N7H, N18D, D32E, Y64C, F85L, E90G, K101R, and N114S amino acid substitutions.

19. The method of claim 1, wherein the mutated mature FGF1 protein comprises SEQ ID NO: 10.

20. The method of claim 1, wherein the mammal is a human.

* * * * *

SEQUENCE LISTING

```
<160> NUMBER OF SEQ ID NOS: 19

<210> SEQ ID NO 1
<211> LENGTH: 468
<212> TYPE: DNA
<213> ORGANISM: Homo sapiens
<220> FEATURE:
<221> NAME/KEY: CDS
<222> LOCATION: (1)..(468)

<400> SEQUENCE: 1 atg gct gaa ggg gaa atc acc acc ttc aca gcc ctg acc gag aag ttt      48
Met Ala Glu Gly Glu Ile Thr Thr Phe Thr Ala Leu Thr Glu Lys Phe
1               5                   10                  15 aat ctg cct cca ggg aat tac aag aag ccc aaa ctc ctc tac tgt agc      96
Asn Leu Pro Pro Gly Asn Tyr Lys Lys Pro Lys Leu Leu Tyr Cys Ser
            20                  25                  30 aac ggg ggc cac ttc ctg agg atc ctt ccg gat ggc aca gtg gat ggg     144
Asn Gly Gly His Phe Leu Arg Ile Leu Pro Asp Gly Thr Val Asp Gly
```

```
                   35                  40                  45
aca agg gac agg agc gac cag cac att cag ctg cag ctc agt gcg gaa      192
Thr Arg Asp Arg Ser Asp Gln His Ile Gln Leu Gln Leu Ser Ala Glu
 50                  55                  60 agc gtg ggg gag gtg tat ata aag agt acc gag act ggc cag tac ttg      240
Ser Val Gly Glu Val Tyr Ile Lys Ser Thr Glu Thr Gly Gln Tyr Leu
 65                  70                  75                  80 gcc atg gac acc gac ggg ctt tta tac ggc tca cag aca cca aat gag      288
Ala Met Asp Thr Asp Gly Leu Leu Tyr Gly Ser Gln Thr Pro Asn Glu
                     85                  90                  95 gaa tgt ttg ttc ctg gaa agg ctg gag gag aac cat tac aac acc tat      336
Glu Cys Leu Phe Leu Glu Arg Leu Glu Glu Asn His Tyr Asn Thr Tyr
            100                 105                 110 ata tcc aag aag cat gca gag aag aat tgg ttt gtt ggc ctc aag aag      384
Ile Ser Lys Lys His Ala Glu Lys Asn Trp Phe Val Gly Leu Lys Lys
        115                 120                 125 aat ggg agc tgc aaa cgc ggt cct cgg act cac tat ggc cag aaa gca      432
Asn Gly Ser Cys Lys Arg Gly Pro Arg Thr His Tyr Gly Gln Lys Ala
130                 135                 140 atc ttg ttt ctc ccc ctg cca gtc tct tct gat taa                      468
Ile Leu Phe Leu Pro Leu Pro Val Ser Ser Asp
145                 150                 155

<210> SEQ ID NO 2
<211> LENGTH: 155
<212> TYPE: PRT
<213> ORGANISM: Homo sapiens

<400> SEQUENCE: 2

Met Ala Glu Gly Glu Ile Thr Thr Phe Thr Ala Leu Thr Glu Lys Phe
  1               5                  10                  15

Asn Leu Pro Pro Gly Asn Tyr Lys Lys Pro Lys Leu Leu Tyr Cys Ser
             20                  25                  30

Asn Gly Gly His Phe Leu Arg Ile Leu Pro Asp Gly Thr Val Asp Gly
         35                  40                  45

Thr Arg Asp Arg Ser Asp Gln His Ile Gln Leu Gln Leu Ser Ala Glu
     50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 3
<211> LENGTH: 468
<212> TYPE: DNA
<213> ORGANISM: Mus musculus
<220> FEATURE:
<221> NAME/KEY: CDS
<222> LOCATION: (1)..(468)

<400> SEQUENCE: 3
```

```
atg gct gaa ggg gag atc aca acc ttc gca gcc ctg acc gag agg ttc      48
Met Ala Glu Gly Glu Ile Thr Thr Phe Ala Ala Leu Thr Glu Arg Phe
1               5                   10                  15 aac ctg cct cta gga aac tac aaa aag ccc aaa ctg ctc tac tgc agc      96
Asn Leu Pro Leu Gly Asn Tyr Lys Lys Pro Lys Leu Leu Tyr Cys Ser
            20                  25                  30 aac ggg ggc cac ttc ttg agg atc ctt cct gat ggc acc gtg gat ggg     144
Asn Gly Gly His Phe Leu Arg Ile Leu Pro Asp Gly Thr Val Asp Gly
        35                  40                  45 aca agg gac agg agc gac cag cac att cag ctg cag ctc agt gcg gaa     192
Thr Arg Asp Arg Ser Asp Gln His Ile Gln Leu Gln Leu Ser Ala Glu
    50                  55                  60 agt gcg ggc gaa gtg tat ata aag ggt acg gag acc ggc cag tac ttg     240
Ser Ala Gly Glu Val Tyr Ile Lys Gly Thr Glu Thr Gly Gln Tyr Leu
65                  70                  75                  80 gcc atg gac acc gaa ggg ctt tta tac ggc tcg cag aca cca aat gag     288
Ala Met Asp Thr Glu Gly Leu Leu Tyr Gly Ser Gln Thr Pro Asn Glu
                85                  90                  95 gaa tgt ctg ttc ctg gaa agg ctg gaa gaa aac cat tat aac act tac     336
Glu Cys Leu Phe Leu Glu Arg Leu Glu Glu Asn His Tyr Asn Thr Tyr
            100                 105                 110 acc tcc aag aag cat gcg gag aag aac tgg ttt gtg ggc ctc aag aag     384
Thr Ser Lys Lys His Ala Glu Lys Asn Trp Phe Val Gly Leu Lys Lys
        115                 120                 125 aac ggg agc tgt aag cgc ggt cct cgg act cac tat ggc cag aaa gcc     432
Asn Gly Ser Cys Lys Arg Gly Pro Arg Thr His Tyr Gly Gln Lys Ala
    130                 135                 140 atc ttg ttt ctg ccc ctc ccg gtg tct tct gac tag                     468
Ile Leu Phe Leu Pro Leu Pro Val Ser Ser Asp
145                 150                 155
```

<210> SEQ ID NO 4
<211> LENGTH: 155
<212> TYPE: PRT
<213> ORGANISM: Mus musculus

<400> SEQUENCE: 4

```
Met Ala Glu Gly Glu Ile Thr Thr Phe Ala Ala Leu Thr Glu Arg Phe
1               5                   10                  15

Asn Leu Pro Leu Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Ala Gly Glu Val Tyr Ile Lys Gly Thr Glu Thr Gly Gln Tyr Leu
65                  70                  75                  80

Ala Met Asp Thr Glu Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

```
<210> SEQ ID NO 5
<211> LENGTH: 140
<212> TYPE: PRT
<213> ORGANISM: Homo sapiens

<400> SEQUENCE: 5

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 6
<211> LENGTH: 155
<212> TYPE: PRT
<213> ORGANISM: Gorilla gorilla

<400> SEQUENCE: 6

Met Ala Glu Gly Glu Ile Thr Thr Phe Thr Ala Leu Thr Glu Lys Phe
1               5                   10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 7
<211> LENGTH: 155
<212> TYPE: PRT
<213> ORGANISM: Pan troglodytes

<400> SEQUENCE: 7
```

```
Met Ala Glu Gly Glu Ile Thr Thr Phe Thr Ala Leu Thr Glu Lys Phe
1               5                   10                  15

Asn Leu Pro Pro Gly Asn Tyr Lys Pro Lys Leu Leu Tyr Cys Ser
            20                  25                  30

Asn Gly Gly His Phe Leu Arg Ile Leu Pro Asp Gly Thr Val Asp Gly
                35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Ile Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 8
<211> LENGTH: 155
<212> TYPE: PRT
<213> ORGANISM: Canis familiaris

<400> SEQUENCE: 8

Met Ala Glu Gly Glu Ile Thr Thr Phe Thr Ala Leu Thr Glu Lys Phe
1               5                   10                  15

Asn Leu Pro Pro Gly Asn Tyr Met Lys Pro Lys Leu Leu Tyr Cys Ser
            20                  25                  30

Asn Gly Gly His Phe Leu Arg Ile Leu Pro Asp Gly Thr Val Asp Gly
                35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
                100                 105                 110

Thr Ser Lys Lys His Ala Glu Lys Asn Trp Phe Val Gly Leu Lys Lys
                115                 120                 125

Asn Gly Ser Cys Lys Arg Gly Pro Arg Thr His Tyr Gly Gln Lys Ala
            130                 135                 140

Ile Leu Phe Leu Pro Leu Pro Val Ser Ser Asp
145                 150                 155

<210> SEQ ID NO 9
<211> LENGTH: 155
<212> TYPE: PRT
<213> ORGANISM: Felis catus

<400> SEQUENCE: 9

Met Ala Glu Gly Glu Ile Thr Thr Phe Thr Ala Leu Thr Glu Lys Phe
1               5                   10                  15
```

```
Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

<210> SEQ ID NO 10
<211> LENGTH: 140
<212> TYPE: PRT
<213> ORGANISM: Artificial Sequence
<220> FEATURE:
<223> OTHER INFORMATION: Mature form of FGF1 with eight point mutations

<400> SEQUENCE: 10

Phe Asn Leu Pro Pro Gly His Tyr Lys Lys Pro Lys Leu Leu Tyr Cys
1               5                   10                  15

Ser Asp Gly Gly His Phe Leu Arg Ile Leu Pro Asp Gly Thr Val Glu
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Cys
50                  55                  60

Leu Ala Met Asp Thr Asp Gly Leu Leu Tyr Gly Ser Gln Thr Pro Asn
65                  70                  75                  80

Glu Glu Cys Leu Leu Leu Glu Arg Leu Gly Glu Asn His Tyr Asn Thr
                85                  90                  95

Tyr Ile Ser Lys Arg His Ala Glu Lys Asn Trp Phe Val Gly Leu Lys
            100                 105                 110

Lys Ser Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 11
<211> LENGTH: 140
<212> TYPE: PRT
<213> ORGANISM: Artificial Sequence
<220> FEATURE:
<223> OTHER INFORMATION: Mature form of FGF1 with five point mutations

<400> SEQUENCE: 11

Phe Asn Leu Pro Pro Gly Asn Tyr Lys Glu Pro Lys Pro Leu Tyr Cys
1               5                   10                  15

Ser Asn Gly Gly His Phe Leu Arg Ile Leu Pro Asp Gly Thr Val Asp
```

```
                      20                  25                  30

Gly Thr Arg Asp Arg Ser Asp Gln His Ile Gln Pro Gln Leu Ser Ala
            35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Thr Ser Lys Lys His Ala Glu Lys Asn Trp Phe Val Gly Leu Lys
            100                 105                 110

Gln Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 12
<211> LENGTH: 140
<212> TYPE: PRT
<213> ORGANISM: Artificial Sequence
<220> FEATURE:
<223> OTHER INFORMATION: Mature form of FGF1 with three point mutations

<400> SEQUENCE: 12

Phe Asn Leu Pro Pro Gly Asn Tyr Lys Lys Pro Lys Leu Leu Tyr Cys
1               5                   10                  15

Ser Asp Arg Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Glu Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 13
<211> LENGTH: 140
<212> TYPE: PRT
<213> ORGANISM: Artificial Sequence
<220> FEATURE:
<223> OTHER INFORMATION: Mature form of FGF1 with a point mutation

<400> SEQUENCE: 13

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45
```

```
Glu Ser Val Gly Glu Val Tyr Ile Lys Ser Thr Glu Thr Gly Gln Tyr
 50                  55                  60

Leu Ala Met Asp Thr Asp Gly Leu Leu Tyr Gly Pro Gln Thr Pro Asn
 65                  70                  75                  80

Glu Glu Cys Leu Phe Leu Glu Arg Leu Glu Glu Asn His Tyr Asn Thr
                 85                  90                  95

Tyr Ile Ser Lys Lys His Ala Glu Lys Asn Trp Phe Val Gly Leu Lys
                100                 105                 110

Lys Asn Gly Ser Cys Lys Arg Gly Pro Arg Thr His Tyr Gly Gln Lys
            115                 120                 125

Ala Ile Leu Phe Leu Pro Leu Pro Val Ser Ser Asp
    130                 135                 140
```

<210> SEQ ID NO 14
<211> LENGTH: 7
<212> TYPE: PRT
<213> ORGANISM: Artificial sequence
<220> FEATURE:
<223> OTHER INFORMATION: Synthetic peptide

<400> SEQUENCE: 14

```
Met Arg Asp Ser Ser Pro Leu
 1               5
```

<210> SEQ ID NO 15
<211> LENGTH: 10
<212> TYPE: PRT
<213> ORGANISM: Artificial sequence
<220> FEATURE:
<223> OTHER INFORMATION: Synthetic peptide

<400> SEQUENCE: 15

```
Ser Tyr Asn His Leu Gln Gly Asp Val Arg
 1               5                  10
```

<210> SEQ ID NO 16
<211> LENGTH: 11
<212> TYPE: PRT
<213> ORGANISM: Artificial sequence
<220> FEATURE:
<223> OTHER INFORMATION: Synthetic peptide

<400> SEQUENCE: 16

```
Ser Tyr Asn His Leu Gln Gly Asp Val Arg Val
 1               5                  10
```

<210> SEQ ID NO 17
<211> LENGTH: 12
<212> TYPE: PRT
<213> ORGANISM: Artificial sequence
<220> FEATURE:
<223> OTHER INFORMATION: Synthetic peptide

<400> SEQUENCE: 17

```
Ser Tyr Asp Tyr Met Glu Gly Gly Asp Ile Arg Val
 1               5                  10
```

<210> SEQ ID NO 18
<211> LENGTH: 56
<212> TYPE: PRT
<213> ORGANISM: Homo sapiens

<400> SEQUENCE: 18

```
Ile Leu Lys Thr Ala Gly Val Asn Thr Thr Asp Lys Glu Met Glu Val
```

```
1               5                   10                  15
Leu His Leu Arg Asn Val Ser Phe Glu Asp Ala Gly Glu Tyr Thr Cys
                20                  25                  30

Leu Ala Gly Asn Ser Ile Gly Leu Ser His His Ser Ala Trp Leu Thr
            35                  40                  45

Val Leu Glu Ala Leu Glu Glu Arg
    50                  55

<210> SEQ ID NO 19
<211> LENGTH: 55
<212> TYPE: PRT
<213> ORGANISM: Homo sapiens

<400> SEQUENCE: 19

Ile Leu Lys His Ser Gly Ile Asn Ser Ser Asp Ala Glu Val Leu Thr
1               5                   10                  15

Leu Phe Asn Val Thr Glu Ala Gln Ser Gly Glu Tyr Val Cys Lys Val
                20                  25                  30

Ser Asn Tyr Ile Gly Glu Ala Asn Gln Ser Ala Trp Leu Thr Val Thr
            35                  40                  45

Arg Pro Ala Leu Glu Glu Arg
    50                  55
```